United States Patent
Anderson et al.

(10) Patent No.: US 7,062,983 B2
(45) Date of Patent: Jun. 20, 2006

(54) SIMULATION APPARATUS

(75) Inventors: Barry Jay Anderson, Cincinnati, OH (US); Michael Joseph Lamping, Cincinnati, OH (US); Eugene Paul Daut, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 137 days.

(21) Appl. No.: 10/422,879

(22) Filed: Apr. 24, 2003

(65) Prior Publication Data

US 2004/0173036 A1 Sep. 9, 2004

Related U.S. Application Data

(63) Continuation-in-part of application No. 10/377,070, filed on Feb. 28, 2003, now Pat. No. 6,843,134.

(60) Provisional application No. 60/429,802, filed on Nov. 27, 2002.

(51) Int. Cl.
*G01M 19/00* (2006.01)
*B30B 15/14* (2006.01)
*B30B 15/16* (2006.01)

(52) U.S. Cl. ........................ 73/866.4; 100/48

(58) Field of Classification Search ................ 73/760, 73/763, 788, 789, 805, 817, 826, 831
See application file for complete search history.

(56) References Cited

U.S. PATENT DOCUMENTS

| | | | |
|---|---|---|---|
| 3,640,127 A * | 2/1972 | Meissner | 73/789 |
| 3,795,134 A * | 3/1974 | Eichenbrenner et al. | 374/50 |
| 4,069,702 A * | 1/1978 | Hayner | 73/11.04 |
| 4,691,576 A * | 9/1987 | Schleuniger et al. | 73/821 |
| 5,188,456 A | 2/1993 | Burke et al. | |
| 5,351,553 A | 10/1994 | Lepie et al. | |
| 5,515,294 A * | 5/1996 | Mohr et al. | 702/113 |

(Continued)

FOREIGN PATENT DOCUMENTS

DE 40 15 178 A1 11/1991

(Continued)

OTHER PUBLICATIONS

Defininitions for "Servomotor" and Servomechanism from American Heritage® Dictionary of the English Language, Third Edition copyright © 1992 by Houghton Mifflin Company, 2 pages.*

(Continued)

*Primary Examiner*—Charles Garber
(74) *Attorney, Agent, or Firm*—George H. Leal; Jay Krebs; Ken Patel

(57) ABSTRACT

A simulation apparatus is provided comprising a fixed main body; a carriage associated with the main body for movement relative to the main body; a first device coupled to the fixed main body for engaging a workpiece; a second device coupled to the carriage for movement with the carriage and for engaging the workpiece; at least one motor apparatus coupled to the fixed main body and the carriage for effecting movement of the carriage and the second device relative to the main body such that a tensile load is applied to the workpiece; sensor apparatus comprising at least one force sensor for sensing the tensile load applied to the workpiece during the movement of the second device; and a drive controller. The controller is coupled to the motor apparatus for controlling the operation of the motor apparatus in accordance with predefined carriage positions corresponding to discrete time intervals and in response to feedback from the sensor apparatus comprising the at least one force sensor so as to enhance the control of the position of the carriage as a function of time.

18 Claims, 21 Drawing Sheets

U.S. PATENT DOCUMENTS

| | | |
|---|---|---|
| 5,575,078 A | 11/1996 | Moulton, III |
| 6,370,962 B1 | 4/2002 | Sullivan et al. |
| 6,410,820 B1 | 6/2002 | McFall et al. |

FOREIGN PATENT DOCUMENTS

| | | |
|---|---|---|
| EP | 1 043 579 A1 | 10/2000 |

OTHER PUBLICATIONS

Thwing-Albert Instrument Company, "Map 3.0 Advanced Script Writing Manual", Programming Manual to Create, Modify and Debug Map 3.0 Software Scripts, pp. 1-69.

* cited by examiner

US 7,062,983 B2

SIMULATION APPARATUS

CROSS-REFERENCE TO RELATED APPLICATION

This application is a continuation-in-part of and claims priority to Application U.S. Ser. No. 10/377,070, entitled 'RING ROLLING SIMULATION PRESS, filed on Feb. 28, 2003, now U.S. Pat. No. 6,843,134, which application is incorporated by reference herein which claims the benefit of 60/429,802 filed Nov. 27, 2002.

BACKGROUND OF THE INVENTION

U.S. Pat. No. 6,370,962 to Sullivan et al. discloses an apparatus for determining the tensile characteristics of a sample under dynamic conditions. The apparatus comprises a housing 16 containing a linear motor 20. The apparatus also comprises a leading jaw assembly 30 and a follower jaw assembly 32, which are mounted to a rail 26 for movement along the rail 26. Further provided are optical sensors 102, 104 and a force sensor 108. Prior to a test run, the jaw assemblies are coupled together, such as using magnets, see column 6, lines 19–20. A sample is mounted in the clamping jaws of the leading and follower jaw assemblies 30 and 32. The "sample S is entered into the test run without being under tensile load," see column 7, lines 14–15. The follower jaw assembly 32 initially moves with the leading jaw assembly 30 until the former reaches catch assemblies 90, at which juncture it stops forward movement. The leading jaw assembly 30 continues movement causing a tensile load to be applied to the sample. It is noted that the linear motor 20 "must achieve the test velocity at the initiation of or prior to the test run," see column 6, lines 34–36. The optical sensors 102, 104 as well as the force sensor 108 generate real-time data during the test run, see column 7, lines 3–6. That data is used to determine stress-strain characteristics of the sample S, see column 7, lines 11–14. It is believed that signals generated by the force sensor 108 are not used by a controller in this apparatus to control the position of either jaw assembly 30, 32 as a function of time.

U.S. Pat. No. 5,188,456 to Burke et al. also discloses an apparatus for determining the tensile characteristics of a sample under dynamic conditions. The apparatus comprises a first gripping jaw 18 coupled to a movable forcer 12. The forcer 12 and, hence, the gripping jaw 18, are moved via a linear stepper motor 10. A second fiber gripping jaw 24 is substantially fixed. It is also coupled to a load cell 32. Prior to a test run, the first jaw 18 is moved in a direction away from the second jaw 24 until an increase in load is sensed by the load cell 32, see column 6, lines 9–12. The first jaw 18 is then moved to a position, as determined by a controller, until the sample is elongated a predefined percentage, see column 6, lines 12–16. The controller then samples the load cell to determine the load on the sample, see column 6, lines 16–19. The '456 patent also contemplates the controller continuously sampling the load cell while the sample is being heated and control the movement of the first jaw 18 so that the load applied to the sample remains constant, see column 6, line 32 through column 7, line 33. It is believed that signals generated by the load cell are not used by the controller in this apparatus to control the position of the first gripping jaw 18 as a function of time.

It is further noted that MTS Systems Corporation produces a material testing system sold under the product name "810 Floor-Standing Systems," see "http://www.mts.com/menusystem.asp?DataSource=0&NodeID=1011." The apparatus comprises a fixed first workpiece gripping member and a movable second workpiece gripping member. The second member is caused to move away from the first member so as to apply a tensile load to a workpiece. Movement of the second member is effected via a servo-valve. The apparatus includes a conventional LVDT sensor for determining relative displacement between the first and second gripping members. It further includes a load sensor for generating signals indicative of the load applied by the workpiece to the first member. It is believed that signals generated by the load sensor are not used by a controller in this apparatus to control the position of the second workpiece gripping member as a function of time.

BRIEF SUMMARY OF THE INVENTION

In accordance with one aspect of the present invention, a simulation apparatus is provided and comprises a fixed main body; a carriage associated with the main body for movement relative to the main body; a first device coupled to the fixed main body for engaging a workpiece; a second device coupled to the carriage for movement with the carriage and for engaging the workpiece; at least one motor apparatus coupled to the fixed main body and the carriage for effecting movement of the carriage and the second device relative to the main body such that a tensile load is applied to the workpiece; sensor apparatus comprising at least one force sensor for sensing the tensile load applied to the workpiece during the movement of the second device; and a drive controller coupled to the at least one motor apparatus for controlling the operation of the at least one motor apparatus in accordance with predefined carriage positions corresponding to discrete time intervals and in response to feedback from the sensor apparatus comprising the at least one force sensor.

It has been found that when the drive controller takes into consideration feedback from the force sensor when controlling the motor apparatus driving the carriage, improved control of the carriage position as a function of time is achieved.

DETAILED DESCRIPTION OF THE INVENTION

Figure 1:
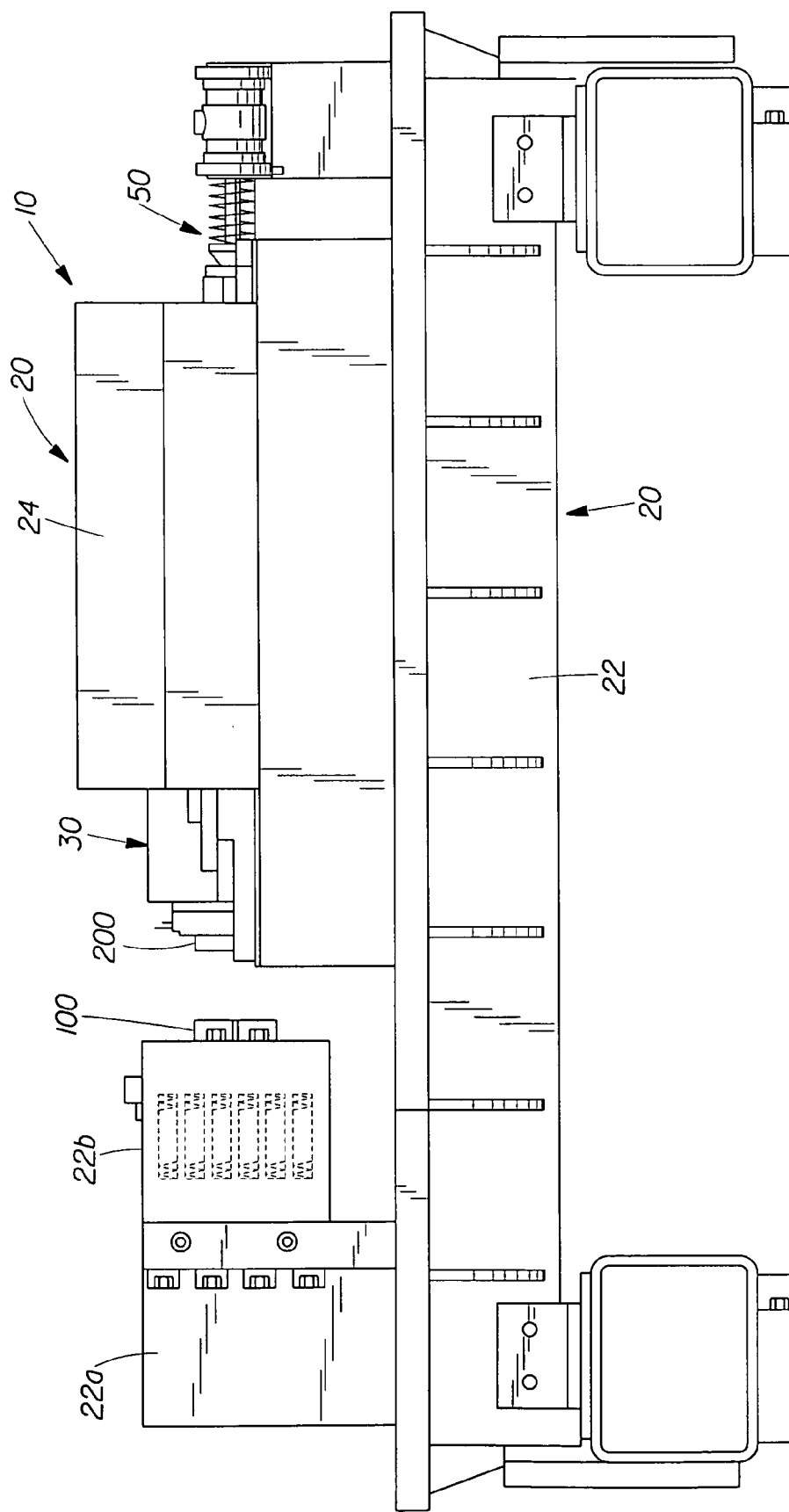
FIG. 1 is a side view of an apparatus of the present invention which functions to conduct a tensile test on a workpiece.

An apparatus 10 constructed in accordance with the present invention for applying a tensile load to a workpiece W is illustrated in FIG. 1. Example workpieces W include polyolefin films and fiber structures; elastomeric films and fiber structures; paper sheets; and other like films and fiber structures. The apparatus 10 comprises a fixed main body 20 comprising a lower portion 22 and an upper portion 24 fixedly coupled to the lower portion 22, see FIGS. 1, 2A and 2B. The apparatus 10 further comprises a linearly reciprocating carriage 30 including a main body portion 34 positioned within a cavity 26 defined by the lower and upper portions 22 and 24 of the main body 20, see FIG. 2A, FIG. 2C (in FIG. 2C, the upper portion 24 has been removed from the lower portion 22 to illustrate the carriage 30), and FIGS. 2D–2G (in FIGS. 2D–2G, only the main body portion 34 is illustrated).

The carriage 30 moves along first and second rails 28a and 28b via conventional linear bearings 32 mounted to a pair of wings 34c forming part of the carriage main body portion 34, see FIGS. 2A, 2C, 2D and 3A and 3B. Reciprocating movement of the carriage 30 is effected via eight separate servo linear motors 40 all working in conjunction, which motors 40 are commercially available from Rockwell International Corporation under the product designation "LEC-S-4P." Each servo motor 40 comprises a generally U-shaped first member 42 comprising a metal U-shaped element 42a having a plurality of magnets 42b mounted within and extending substantially the entire length of its U-shaped cavity, see FIGS. 2A and 4, and a movable second member 43 comprising a metal support plate having a plurality of coils wrapped about and extending along the length of the support plate, see FIGS. 2H and 21. Four of the first members 42 are fixedly coupled to an inner surface 24a of the upper portion 24 of the main body 20, see FIG. 2A, while the remaining four first members (not shown) are fixedly coupled to an upper surface (not shown) of the lower portion 22 of the main body 20 just below the carriage 30. Four of the second members 43 are fixedly coupled to an upper portion 34a of a main plate 34d of the carriage main body portion 34, while the remaining four second members (not shown) are fixedly coupled to a lower portion 34b of the main plate 34d of the carriage main body portion 34. Four polymeric alignment plates 44 are mounted to the upper portion 34a of the main plate 34d, see FIG. 2A, and four polymeric alignment plates (not shown) are mounted to the lower portion 34b of the main plate 34d. The motor second members 43, fixedly coupled to the upper and lower portions 34a and 34b of the main plate 34d of the carriage main body portion 34, are mounted inline with the polymeric plates 44. Upon actuation of the motors 40, each second member 43 moves relative to its corresponding first member 42 such that the carriage 30 linearly moves relative to the fixed main body 20. In the illustrated embodiment, the motors 40 are capable of moving the carriage 30 at a speed up to +/−3 meters/second, and at an acceleration rate up to +/−196 m/s$^2$, and cause the carriage 30 to generate a tensile load upon a workpiece W, i.e., the force applied by first and second gripping devices 100 and 200 to the workpiece W of up to about +/−20,000 Newtons.

Figure 10:
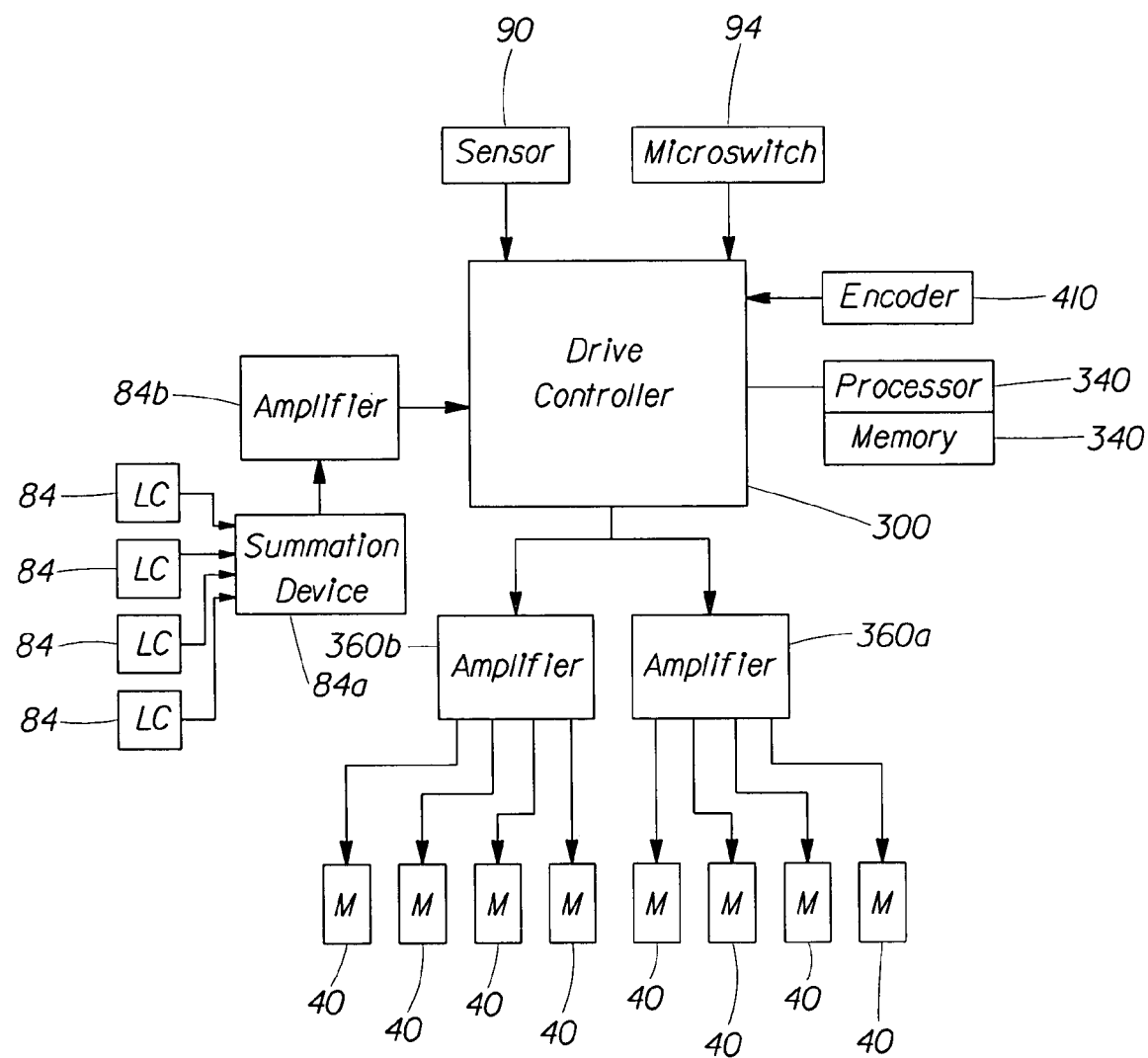
FIG. 10 is a block diagram illustrating a driver controller and amplifiers for driving the motors of the apparatus of FIG. 1.

A drive controller 300, one of which is commercially available from Delta Tau Corporation under the product designation "Turbo PMAC 2-PC," is provided for controlling the operation of the motors 40, see FIG. 10. The drive controller 300 generates a drive signal, which is received by first and second amplifiers 360a and 360b. The amplifiers 360a and 360b are commercially available from Delta Tau Corporation under the product designation "Quad Amp." Each amplifier 360a, 360b is connected to four servo motors 40. In response to receiving the drive signal from the controller 300, each amplifier 360a, 360b generates substantially the same drive control signal to its corresponding four motors 40.

Figure 2A:
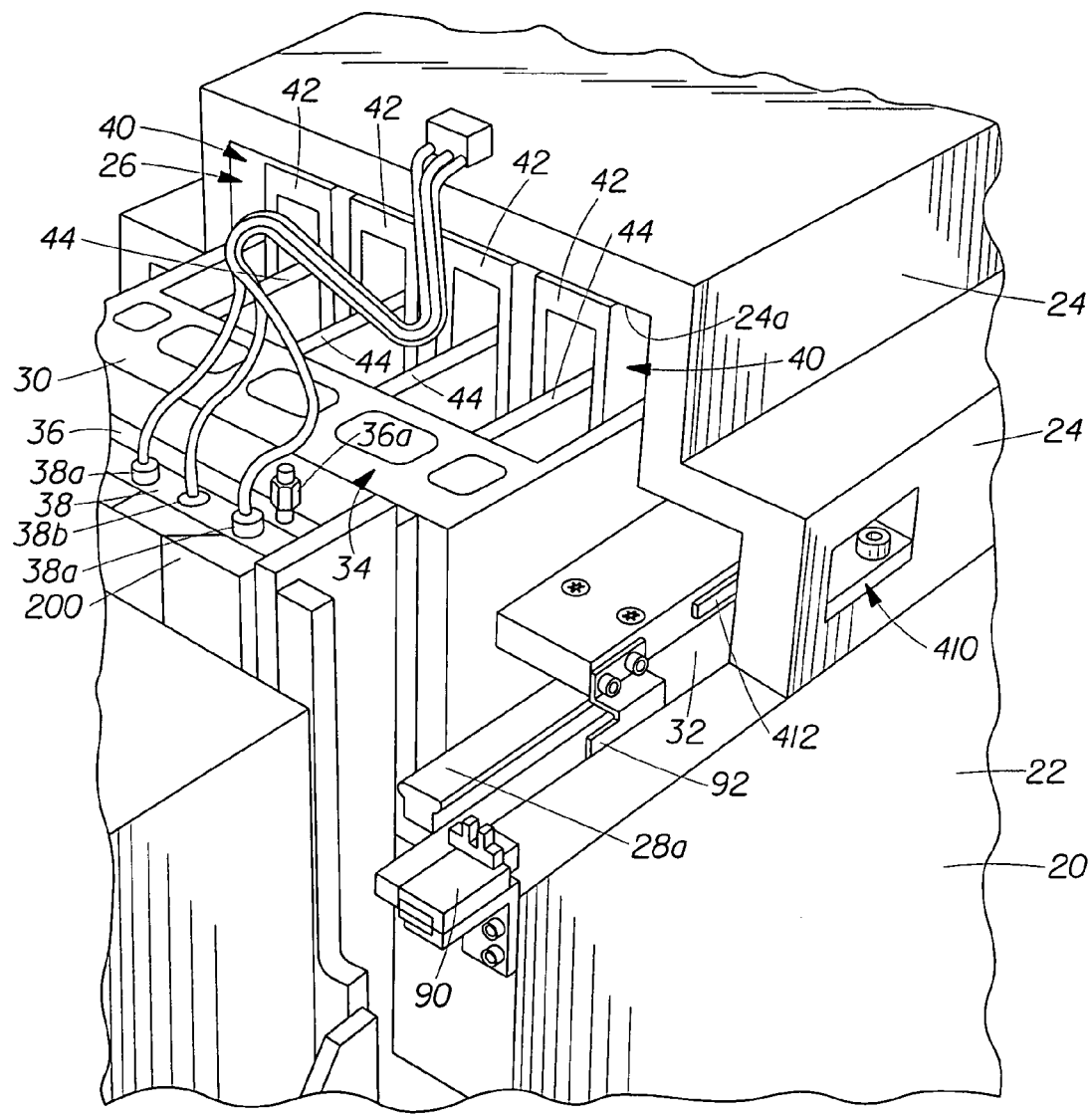
FIG. 2A is a perspective view illustrating a reciprocating carriage provided with a second gripping device, wherein the carriage is positioned within a cavity defined by the upper and lower portions of a main body of the apparatus.
Figure 2B:
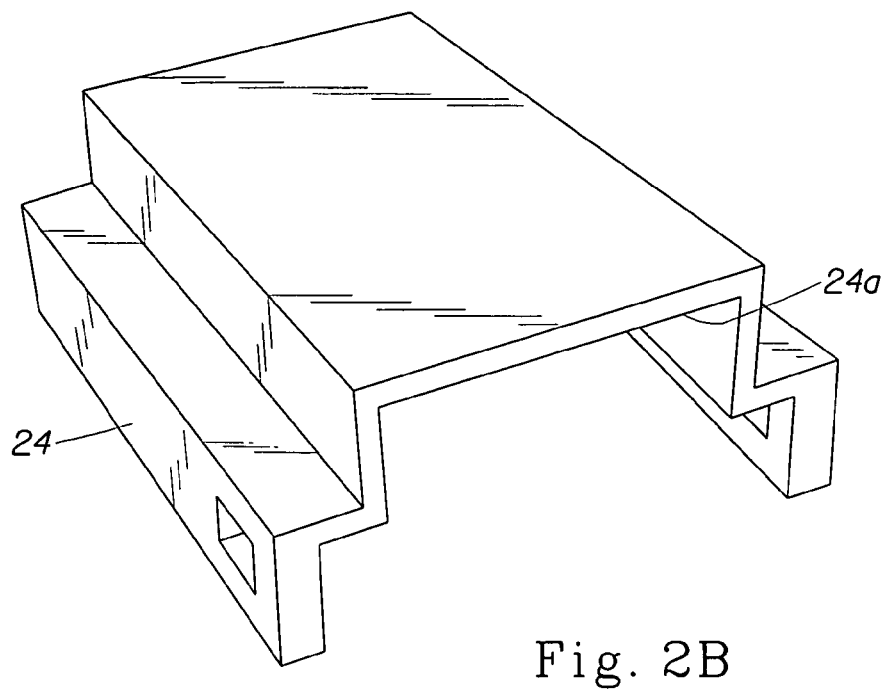
FIG. 2B is a perspective view of the upper portion of the apparatus main body.
Figure 2C:
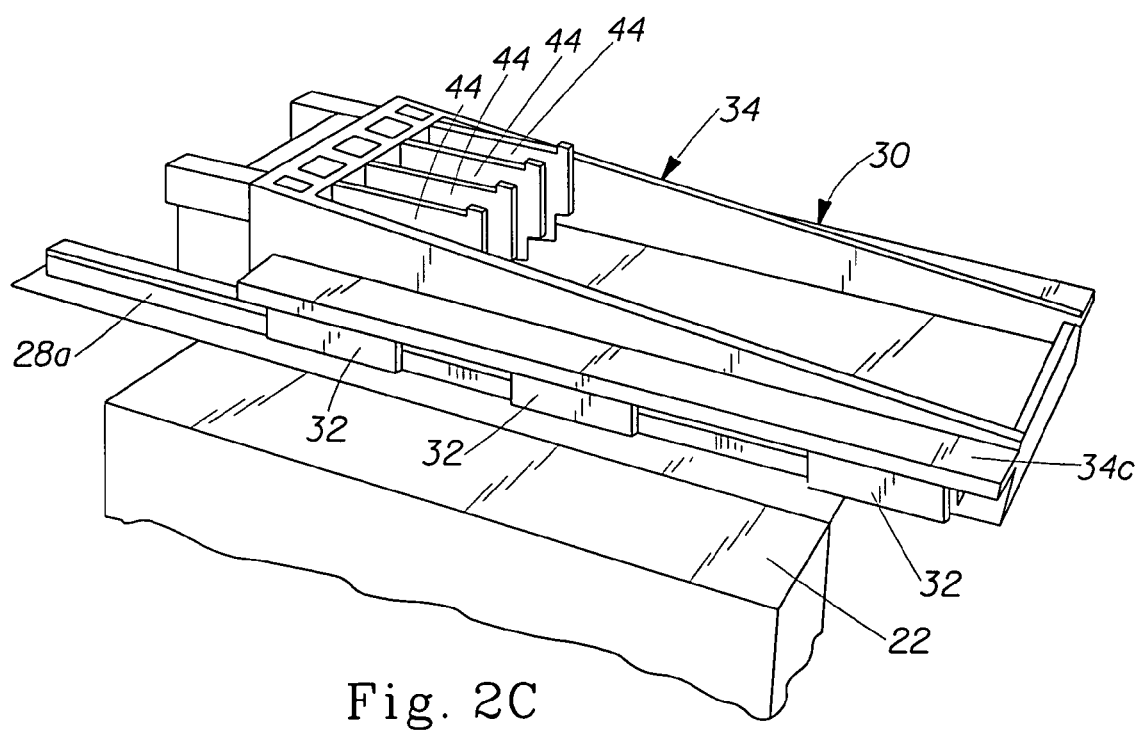
FIG. 2C is a perspective side view of the carriage mounted to the main body lower portion and wherein the main body upper portion and linear servo motors have been removed.
Figure 2D:
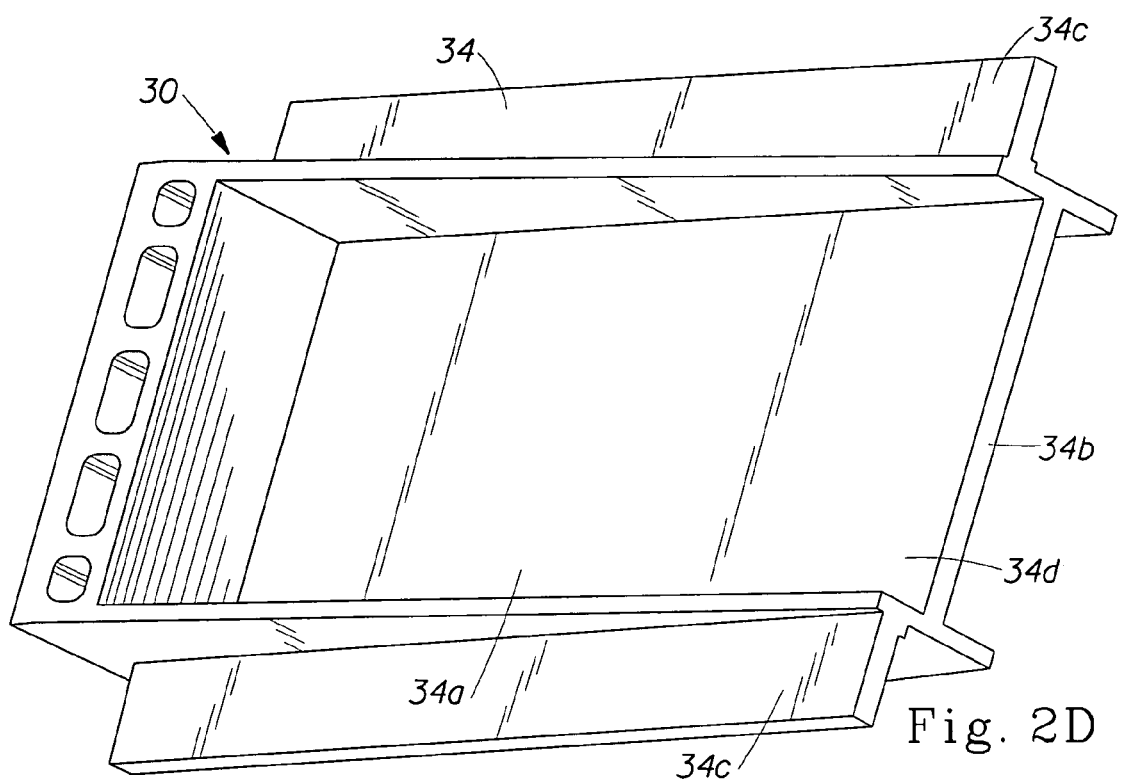
FIG. 2D is perspective view of the carriage main body.
Figure 2E:
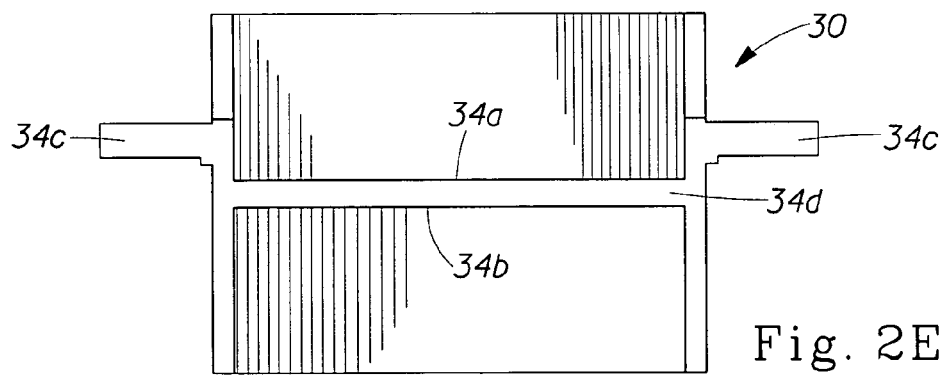
FIG. 2E is a rear view of the carriage main body.
Figure 2F:
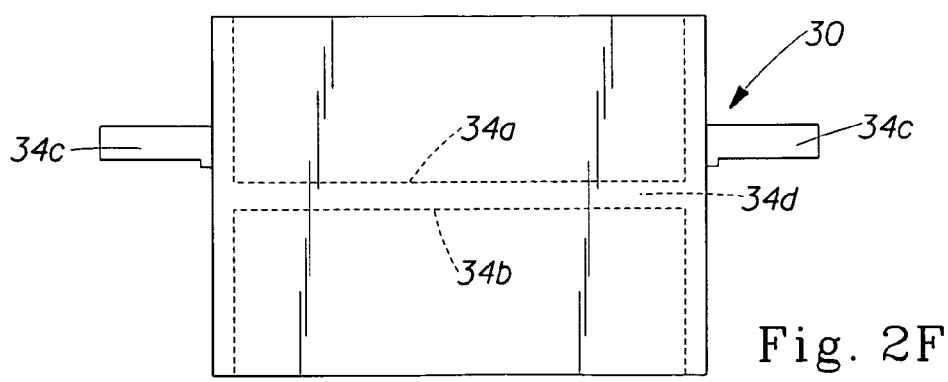
FIG. 2F is a front view of the carriage main body.
Figure 2G:
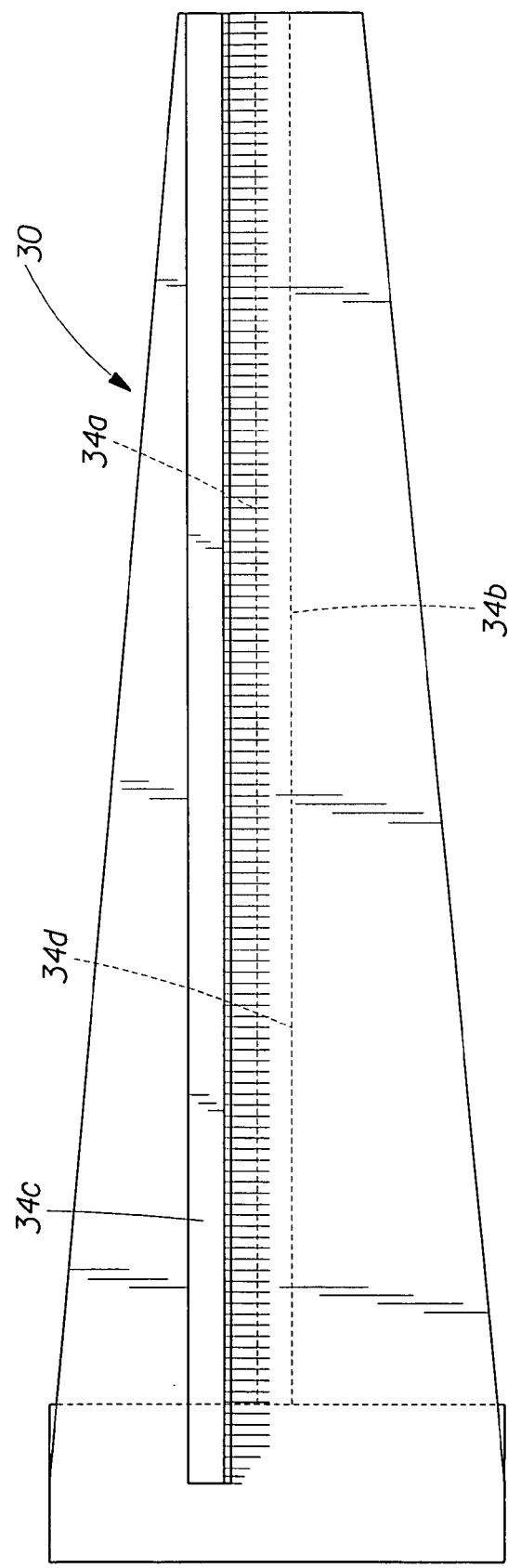
FIG. 2G is a side view of the carriage main body.
Figure 2H:
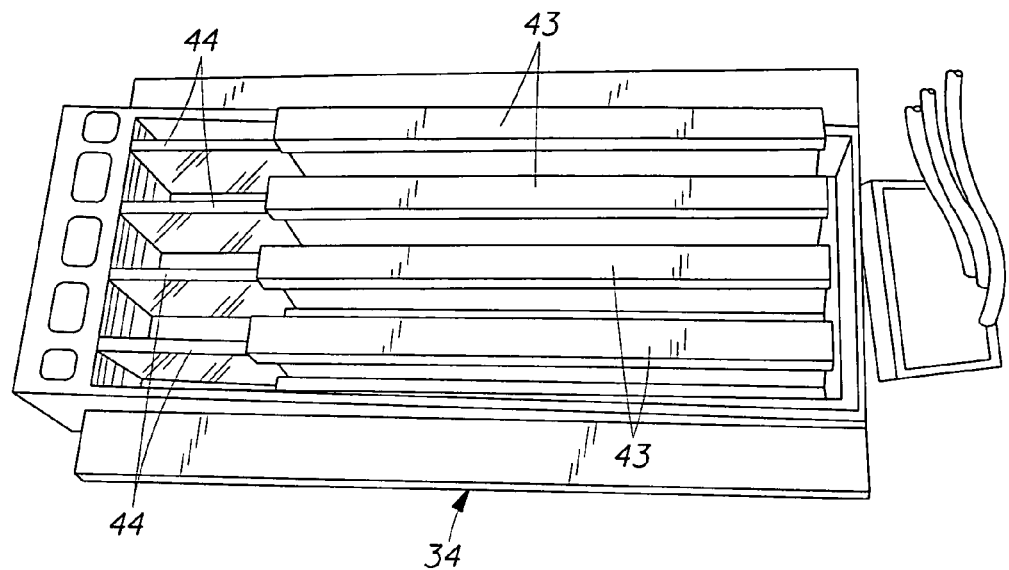
FIG. 2H is a perspective view of the carriage and motor second members.
Figure 2I:
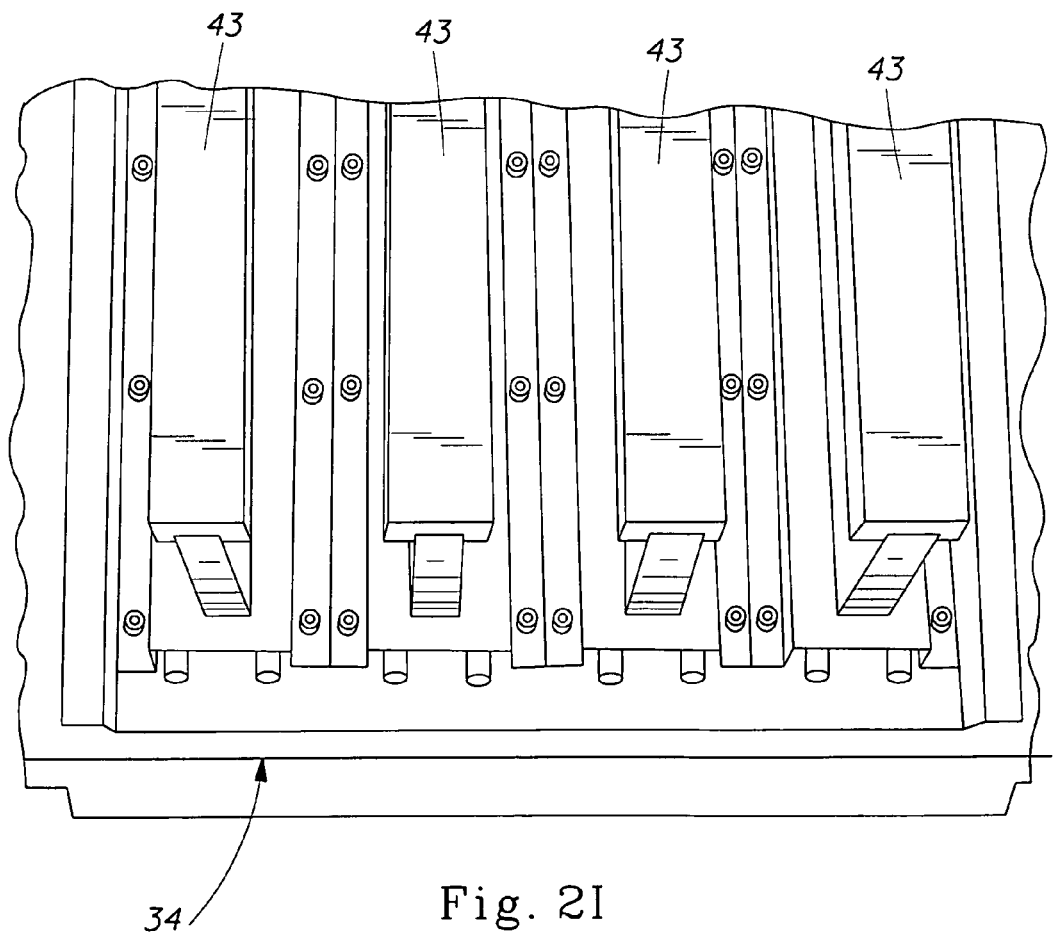
FIG. 2I is a perspective view of a portion of the carriage and motor second members.

The position of the carriage 30 relative to the fixed main body 20 is sensed via a linear encoder read head 410 coupled to the upper portion 24 of the fixed main body 20, see FIG. 2A, which reads a position value from a corresponding sensor strip 412 mounted to the carriage 30 for movement with the carriage 30.

Figure 3A:
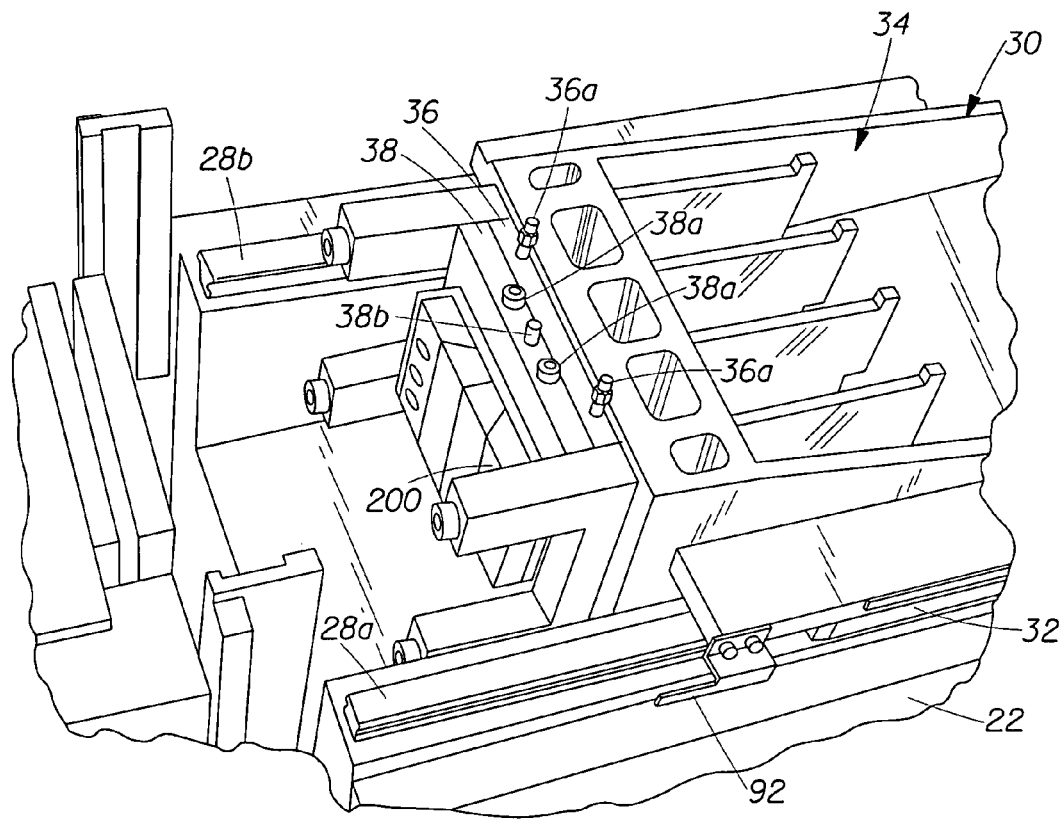
FIG. 3A is a perspective view of a portion of the carriage and the second gripping device mounted to the carriage.
Figure 3B:
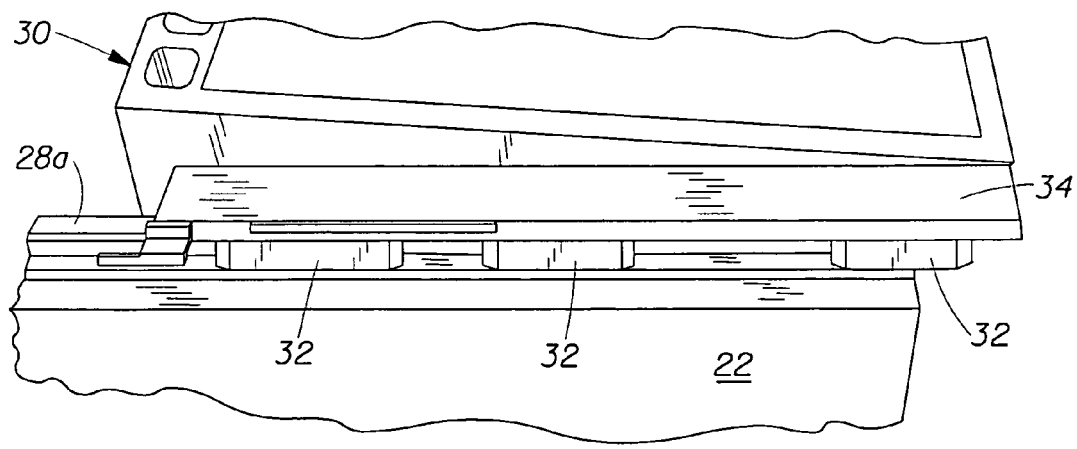
FIG. 3B is a side, perspective view of a portion of the carriage and a portion of the main body lower portion.
Figure 4:
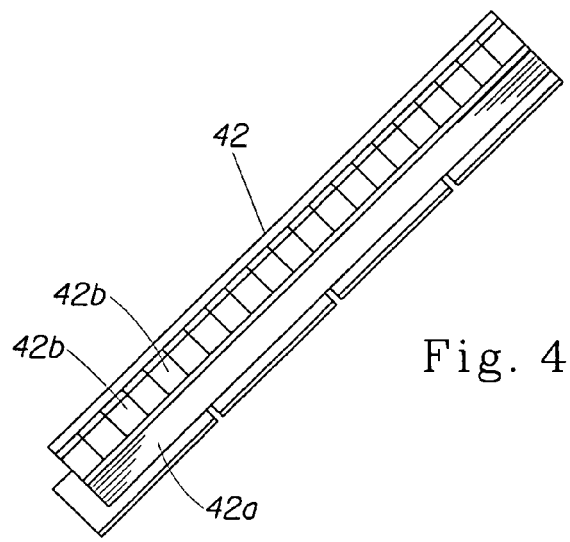
FIG. 4 is a perspective view of a U-shaped first member of one of the servo linear motors in the apparatus of FIG. 1.
Figure 8A:
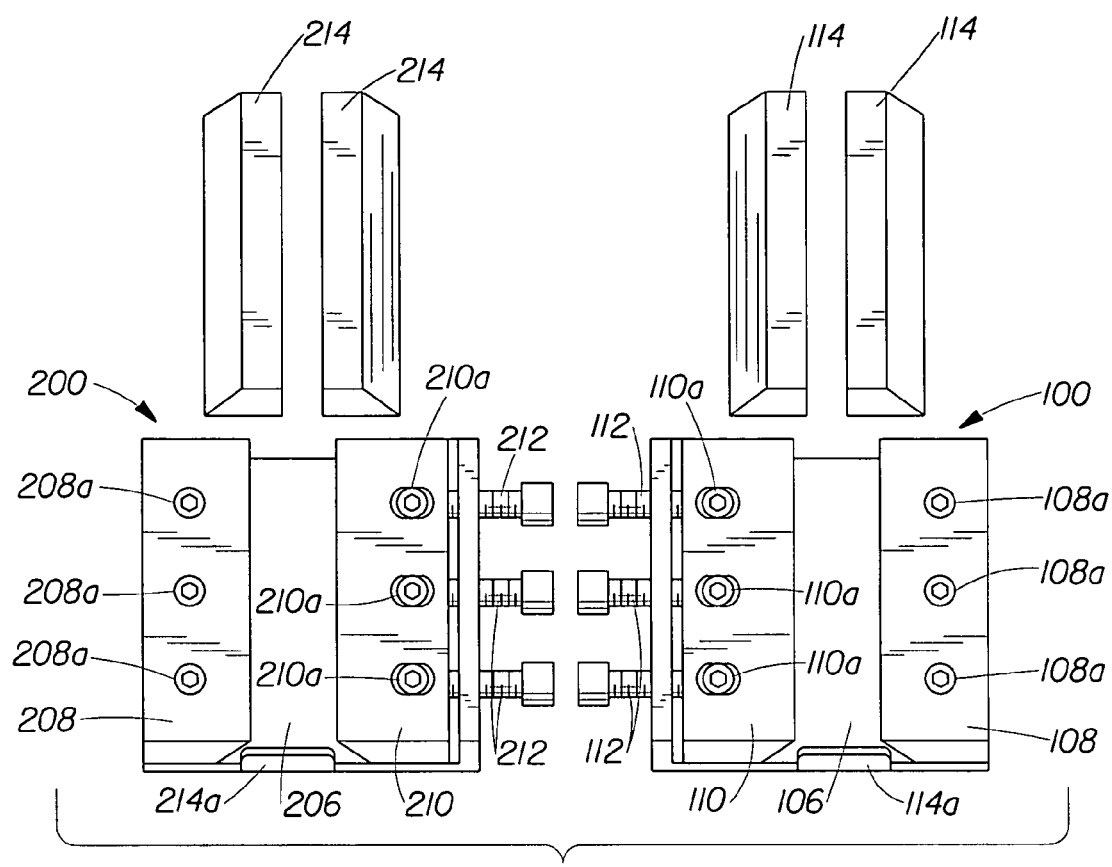
FIGS. 8A–8D are views of the first and second gripping devices.
Figure 8B:
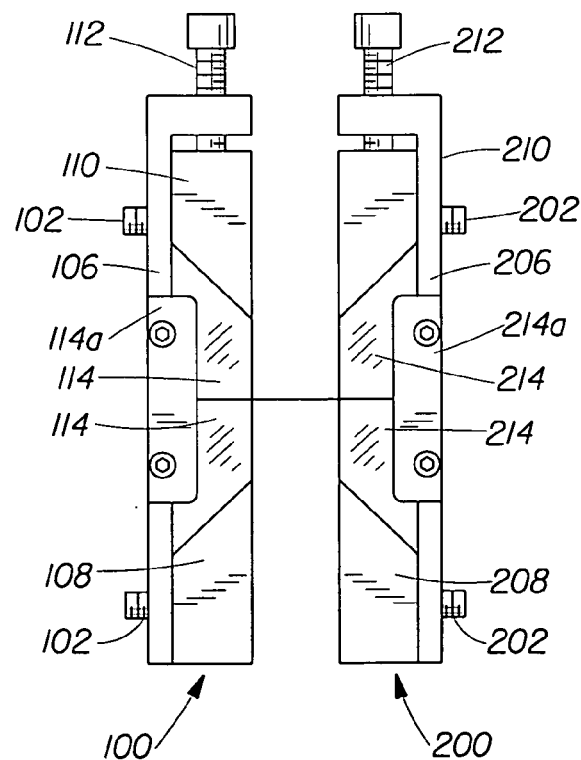
Figure 10A:
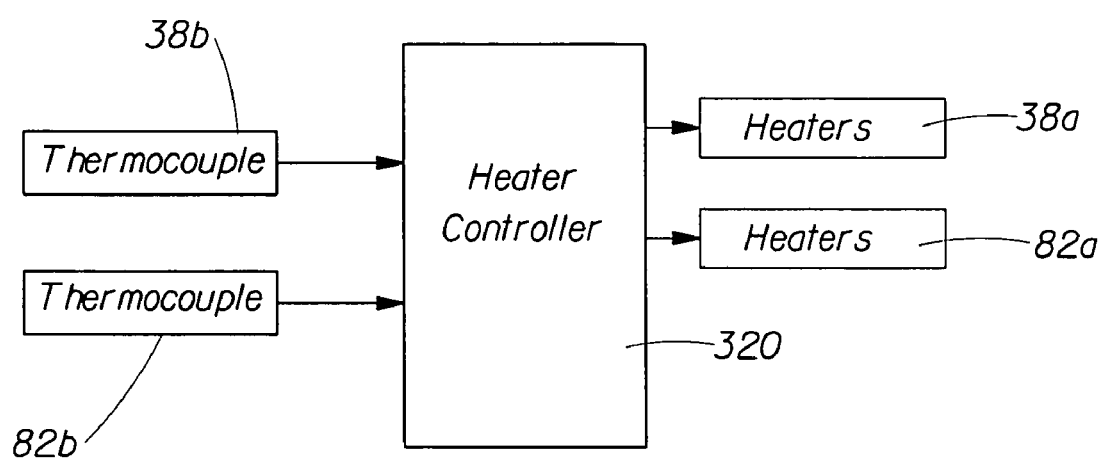
FIG. 10A is a block diagram illustrating a heater controller of the present invention.

The carriage 30 further comprises a cooled plate 36 and a heated plate 38, see FIGS. 2A and 3A. The second gripping device 200 is mounted by bolts 202 directly to the heated plate 38, see FIGS. 3A, 8B and 8D. The plate 38 is heated via a pair of resistive heaters 38a, see FIGS. 2A and 3A. The temperature of the plate 38 is detected via a thermocouple 38b, which generates temperature signals to a heater controller 320, see FIGS. 2A and 10A. The heater controller 320 controls activation of the resistive heaters 38a so as to maintain the plate 38 at a desired temperature. The cooled plate 36 is cooled via air circulating through the plate 36.

The air is provided to the plate 36 via a pair of air lines coupled to the plate 36 via fittings 36a, see FIG. 3A. The cooled plate 36 prevents energy in the form of heat from being transferred from the heated plate 38 to the carriage main body portion 34.

A pair of spring-biased rear bumpers 50 is provided to limit the travel of the carriage 30 in a direction away from the first gripping device 100, see FIG. 1.

Referring again to FIG. 1, the lower portion 22 of the main body 20 comprises an outer support member 22a. Extending through the support member 22a are, in the illustrated embodiment, four threaded bores (not shown), each provided with a corresponding threaded rod 60, see FIGS. 6 and 7. Fixedly coupled to the outer support member 22a are a pair of L-shaped position limiting members 22b and 22c. A spring-loading plate 70 is received between the members 22b and 22c and abuts against the threaded rods 60. A spring-loaded base plate 72 is also received between the members 22b and 22c and is biased against arm portions 22d of the limiting members 22b and 22c via a plurality of compression springs 74, see FIGS. 5–7 and 6A. A pair of alignment rods 72a extend from the plate 72 and pass through linear bearings 70a provided in the spring-loading plate 70 as well as linear bearings (not shown) provided in the support member 22a, see FIG. 7. The springs 74 are mounted on corresponding rods extending from the spring-loaded plate 72. Bores are provided in the spring-loading plate 70 for receiving the rods about which the springs 74 are mounted. The position of the spring-loading plate 70 can be varied via adjustment of the positions of the threaded rods 60 so as to adjust the biasing force applied by the springs 74 against the plate 72. In the illustrated embodiment, approximately twelve (12) springs 74 are provided for applying approximately 7000 pounds (31,000 N) of force against the spring-loaded plate 72.

A cooled plate 80 is fixedly coupled to the spring-loaded plate 72 via bolts (not shown), see FIGS. 5–7 and 6A. A heated plate 82 is fixedly mounted to the cooled plate 80 via preload screws. Positioned between the cooled plate 80 and the heated plate 82 are a plurality of piezoelectric load cells 84, four in the illustrated embodiment, see FIGS. 6A and 7, which are commercially available along with the preload screws for joining the heated plate 82 to the cooled plate 80 from Kistler Instrument Corporation under the product designation "Load Washer and Preload Screw, Model No. 9031." Signals generated by the load cells 84 are provided to a summation device 84a, see FIG. 10, which is commercially available from Kistler Corporation under the product designation "4-Gang Connector, Model No. 107B." The summation device 84a functions to combine the signals generated by the four load cells 84 and generate a single force signal to an amplifier 84b. The amplifier 84b is commercially available from Kistler Corporation under the product designation "Dual Charge Amplifier, Model No. 5010B." An amplified force signal is generated by the amplifier 84b to the controller 300 and is representative of the combined compressive force directly applied to the load cells 84 by the cooled and heated plates 80 and 82. The preload screws coupling the heated plate 82 to the plate 80 extend through center bores in the load cells 84. Each of the four load cells 84 is preloaded with 3000 pounds (13,345 N) of load, for a combined preload on the four load cells 84 of 12,000 pounds (53,375 N). Since the load cells 84 are preloaded, when a tensile load is applied to a workpiece W by the first and second gripping devices 100 and 200, the compressive load applied to the load cells 84 by the cooled and heated plates 80 and 82 is reduced. This reduction in compressive load applied to the load cells 84 is equal to the tensile load applied to the workpiece W by the first and second gripping devices 100 and 200. The magnitude of the tensile load applied to the workpiece W is also equal to the magnitude of the tensile load applied by the workpiece W to each of the first and second gripping devices 100 and 200 and the carriage 30.

Figure 5:
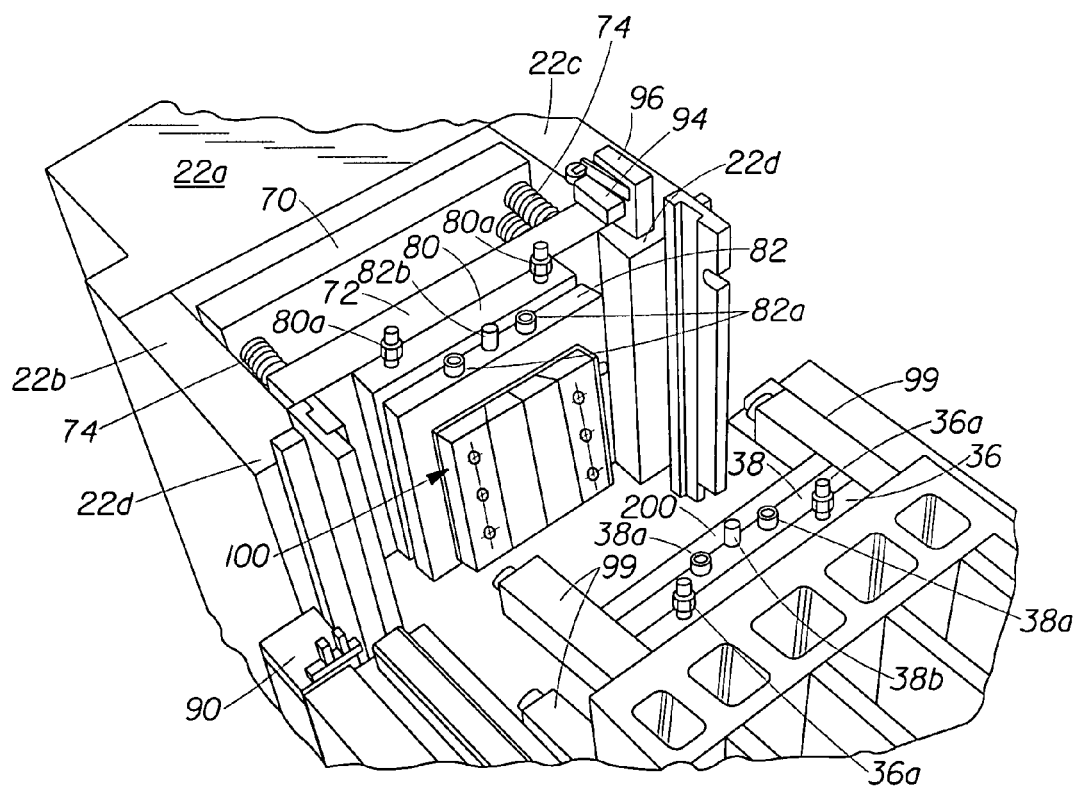
FIG. 5 is a perspective view of an outer support member of the apparatus main body, L-shaped position limiting members; a spring-loading plate, a spring-loaded plate, a heated plate, a cooled plate and a stationary first gripping device of the apparatus illustrated in FIG. 1.
Figure 5A:
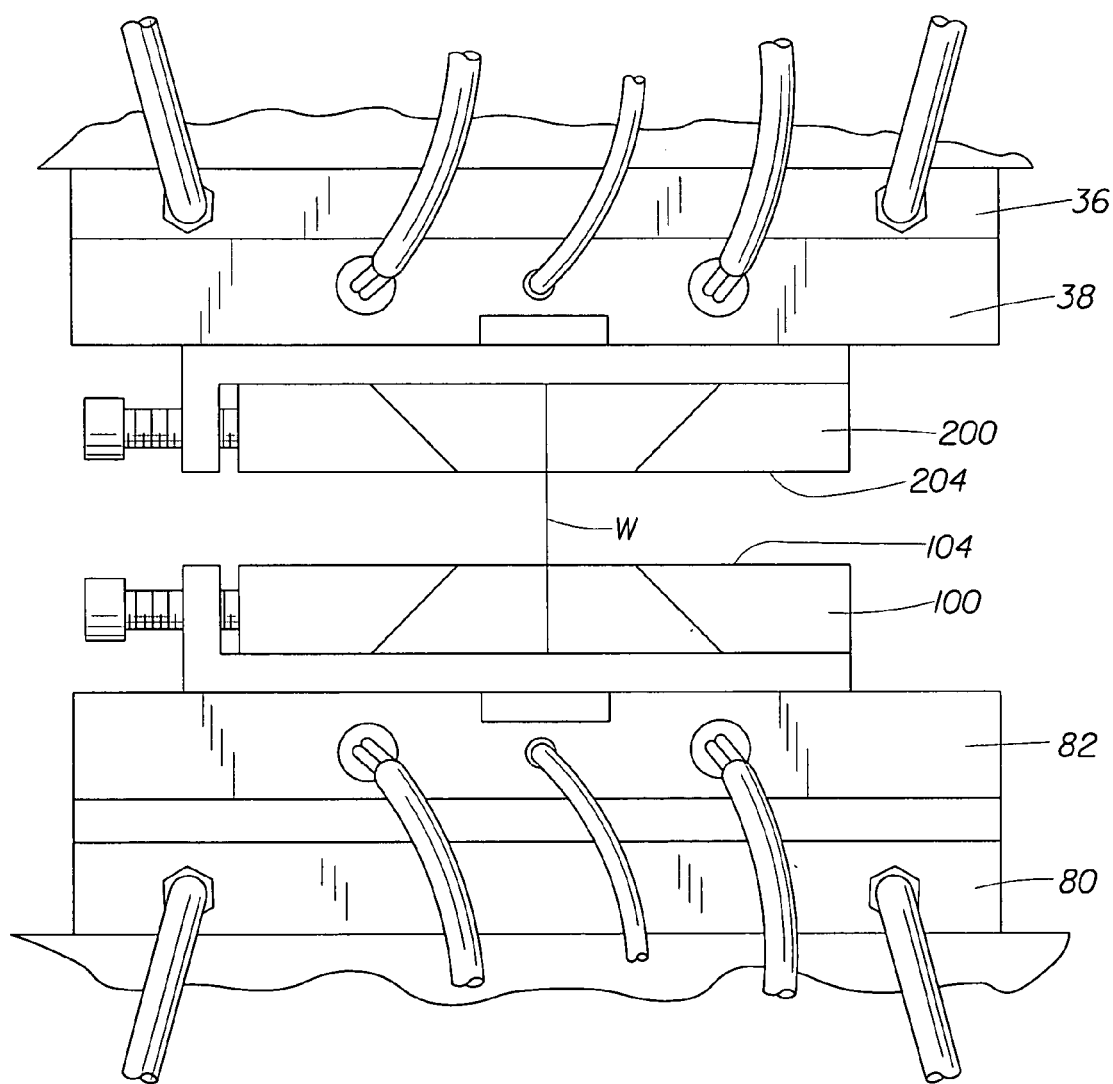
FIG. 5A is a top view of the first and second gripping devices having a workpiece clamped therein.
Figure 6:
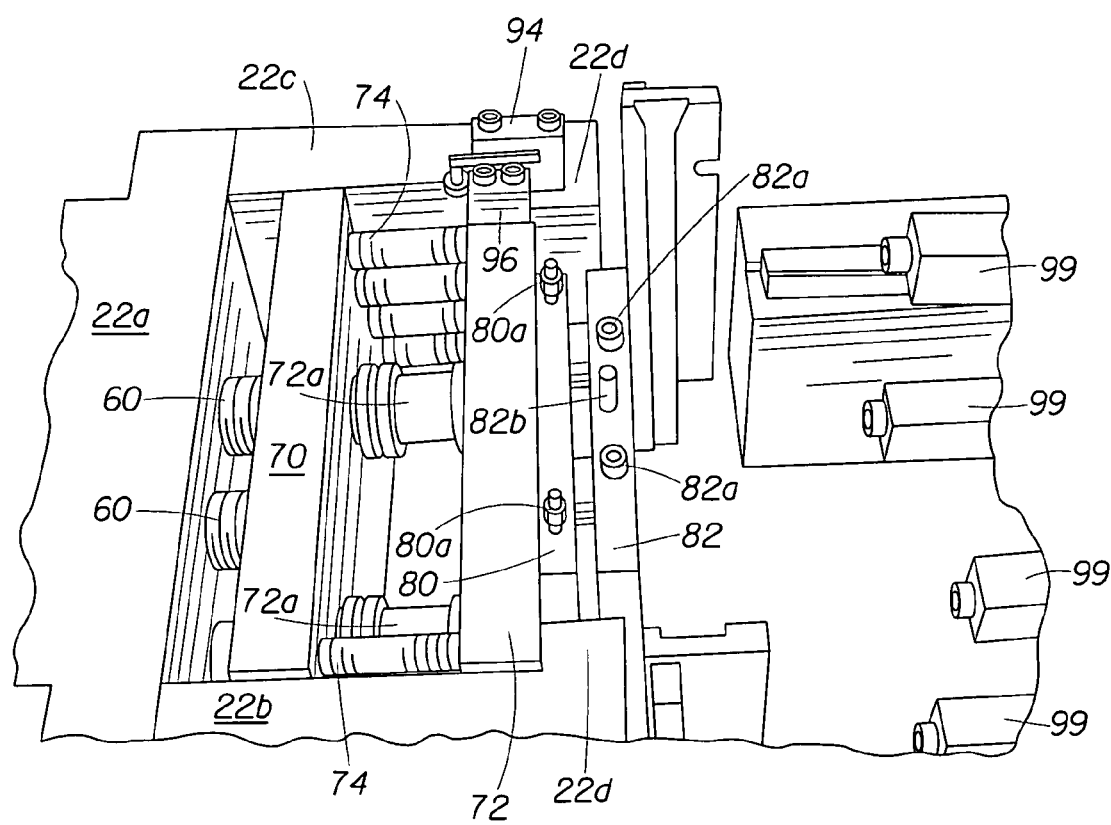
FIGS. 6 and 7 are perspective views of the outer support member of the apparatus main body, the L-shaped position limiting members, the spring-loading plate, the spring-loaded plate, the heated plate, and the cooled plate and, wherein the stationary first gripping device is not illustrated.
Figure 6A:
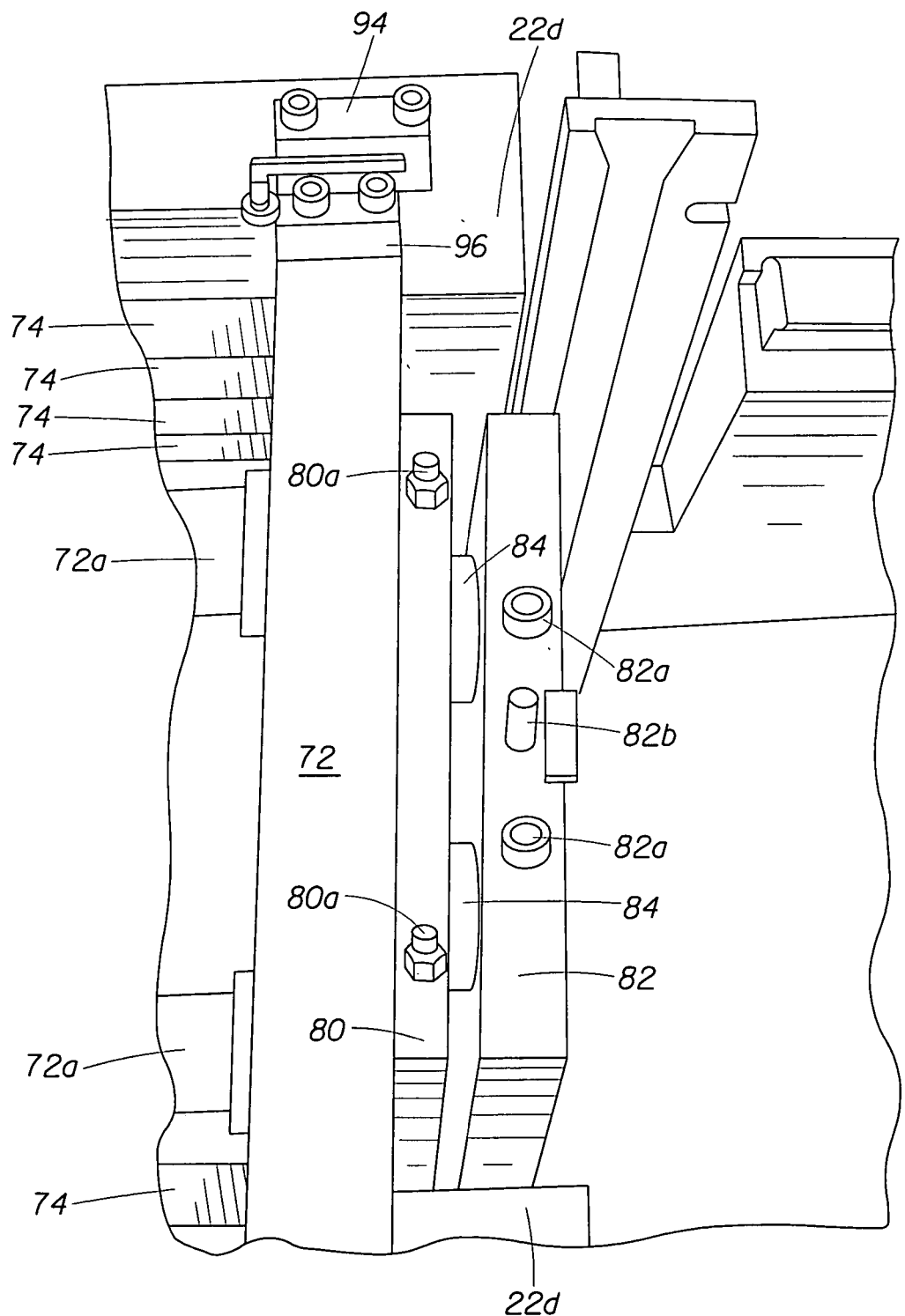
FIG. 6A is a perspective view of portions of the L-shaped position limiting members; the spring-loaded plate, the heated plate, and the cooled plate and, wherein the stationary first gripping device is not illustrated.
Figure 7:
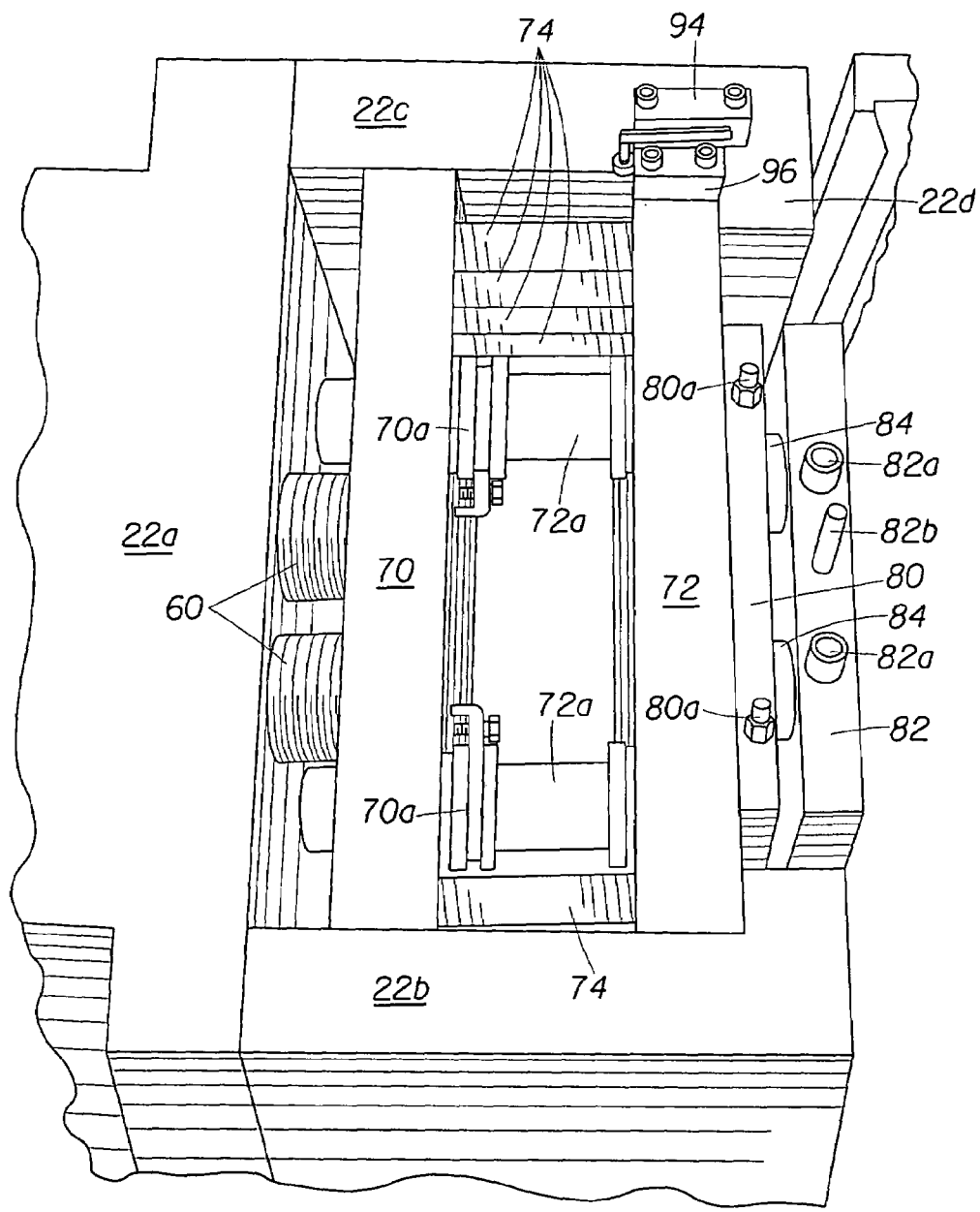

The first gripping device 100, illustrated in FIGS. 5, 5A, 8B and 8D, but not shown in FIGS. 6, 7 and 6A, is mounted by bolts 102 directly to the heated plate 82. The plate 82 is heated via a pair of resistive heaters 82a, see FIGS. 5, 6 and 6A. The temperature of the plate 82 is detected via a thermocouple 82b, which generates temperature signals to the controller 320, see FIGS. 6, 6A and 10A. The heater controller 320 controls activation of the resistive heaters 82a so as to maintain the plate 82 at a desired temperature. The cooled plate 80 is cooled via air circulating through the plate 80. The air is provided to the plate 80 via a pair of air lines coupled to the plate 80 via fittings 80a. The cooled plate 80 prevents energy in the form of heat from being transferred from the heated plate 82 to the spring-loaded plate 72.

To prevent damage to the first and second gripping devices 100 and 200 due to over travel of the carriage 30 towards the first gripping device 100, a sensor 90 is mounted to the lower portion 22 of the main body 20 and a flag 92 is mounted to the main body portion 34 of the carriage 30, see FIGS. 2A, 3A and 5. The sensor 90 is coupled to the controller 300, see FIG. 10. If the carriage 30 moves too far in a direction towards the first gripping device 100, the flag 92 on the carriage 30 will actuate the sensor 90, which generates a corresponding signal to the controller 300. In response, the controller 300 terminates power to the motors 40 driving the carriage 30. A second sensor arrangement for preventing damage to the first and second gripping devices 100 and 200 is also provided. It comprises a microswitch 94 mounted to the limiting member 22c and an actuator 96 fixedly mounted to the spring-loaded plate 72, see FIGS. 6 and 7. The microswitch 94 is coupled to the controller 300, see FIG. 10. Engagement arms 99 (not shown in FIGS. 2A, 2D–2G and 5A) are mounted to the main body portion 34 of the carriage 30, see FIGS. 5 and 6, and are adapted to engage the spring-loaded plate 72 just prior to the second gripping device 200 engaging the first gripping device 100. When the force applied by the engagement arms 99 against the spring-loaded plate 72 exceeds the biasing force applied by the compression springs 74 against the plate 72, the plate 72 will move in a direction toward the spring-loading plate 70 causing the actuator 96 to actuate the switch 94, which, in turn, generates a corresponding signal to the controller 300. In response, the controller 300 disconnects power to the motors 40 driving the carriage 30.

In accordance with the present invention, a tensile load is applied to a workpiece W by the first and second gripping devices 100 and 200 such that the workpiece W experiences a predefined substantially constant rate of strain. The tensile load is applied to the workpiece W until the workpiece fails or the carriage 30 reaches the end of its stroke or run, e.g., about 75 mm from the rear bumpers 50.

The first workpiece gripping device 100 comprises a support plate 106, which is coupled directly to the heated plate 82 via bolts 102, see FIGS. 5, 5A and 8A–8D. An outer member 108 is fixed to the support plate 106 by bolts 108a, see FIG. 8A. A movable outer member 110 is coupled to the support plate 106 by bolts 110a and 112. Positioned between the outer members 108 and 110 are removable, workpiece-engaging members 114. Once a workpiece W has been positioned between the engaging members 114, the engaging members 114 are inserted between the outer members 108 and 110. A stop 114a is provided to limit the travel of the engaging members 114 when they are inserted between the outer members 108 and 110. The bolts 112 are then adjusted by an operator causing the outer member 110 to move toward the fixed member 108 so as to lock the workpiece W between the engaging members 114 and 116.

The second workpiece gripping device 200 comprises a support plate 206, which is coupled directly to the heated plate 38 via bolts 202, see FIGS. 2A and 8A–8D. An outer member 208 is fixed to the support plate 206. A movable outer member 210 is adjustably coupled to the support plate 206 by bolts 210a and 212. Positioned between the outer members 208 and 210 are removable, workpiece-engaging members 214. Once a workpiece W has been positioned between the engaging members 214, the engaging members 214 are inserted between the outer members 208 and 210. A stop 214a is provided to limit the travel of the engaging members 214 when they are inserted between the outer members 208 and 210. The bolts 212 are then adjusted by an operator causing the outer member 210 to move toward the fixed member 208 so as to lock the workpiece W between the engaging members 214.

Figure 12:
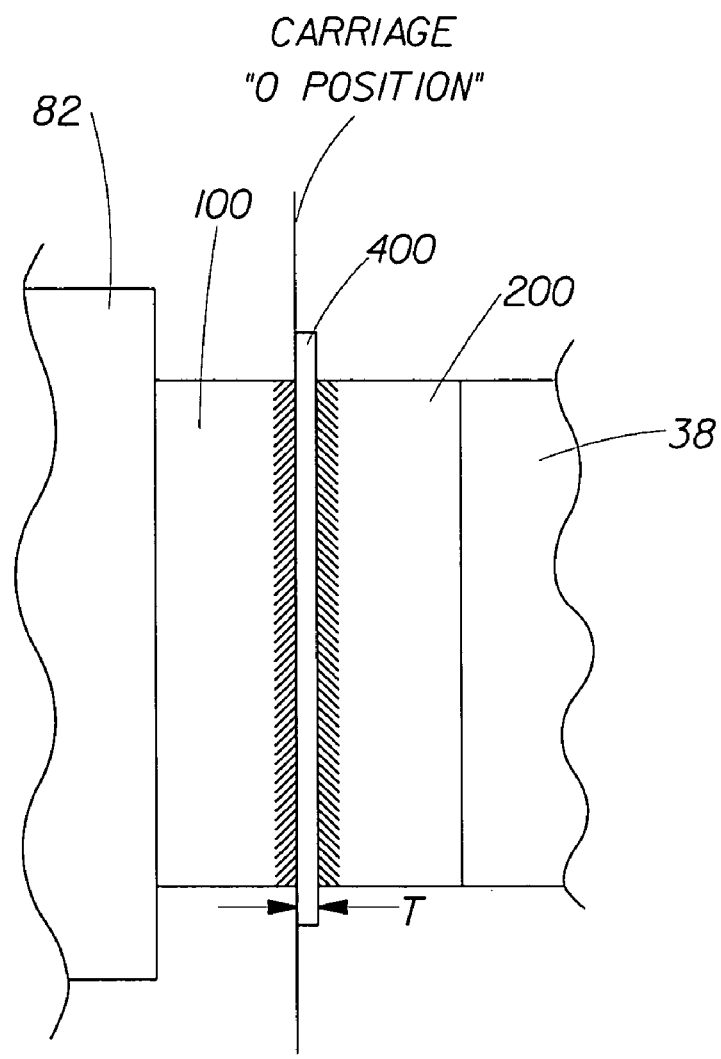
FIG. 12 is a schematic side view of a calibration plate being engaged by the first and second gripping devices of the apparatus of FIG. 1.

Prior to conducting a tensile test operation, a "home" position is determined for the carriage 30. Without a workpiece W clamped between the first and second gripping devices 100 and 200, the controller 300 causes the second gripping device 200 to slowly move toward the first gripping device 100 until it engages a calibration plate 400, having a known thickness T, positioned adjacent to the first gripping device 100, see FIG. 12. The controller 300 controls the movement of the second gripping device 200 so that it slowly moves toward the first gripping device 100 until it engages the calibration plate 400. At the point of engagement, a position error of the servo linear motors 40 increases because movement of the carriage 30 is blocked by the calibration plate 400, which increase in position error is detected by the controller 300. That is, the controller 300 determines from position signals generated by the linear encoder read head 410 that the position of the carriage 30 is not changing even though the controller 300 is generating a drive signal to provide power to the motors 40. In response to sensing 0 movement of the carriage 30, the controller 300 knows that the carriage 30 is positioned a distance equal to the thickness of the calibration plate 400 away from a "0 position" for the carriage 30, i.e., the position of the carriage 30 if the second gripping device 200 were allowed to engage the first gripping device 100. The controller 300, based upon a position signal generated by the linear encoder read head 410 after reading the corresponding position value from the sensor strip 412, defines the current position of the carriage 30 as being a distance away from the "0 position" equal to the thickness of the calibration plate 400. As will be discussed further below, the controller 300 defines the "home" position of the carriage 30 as the position of the carriage 30 when the second gripping device 200 is positioned a distance "Pli" away from the first gripping device 100.

Figure 8C:
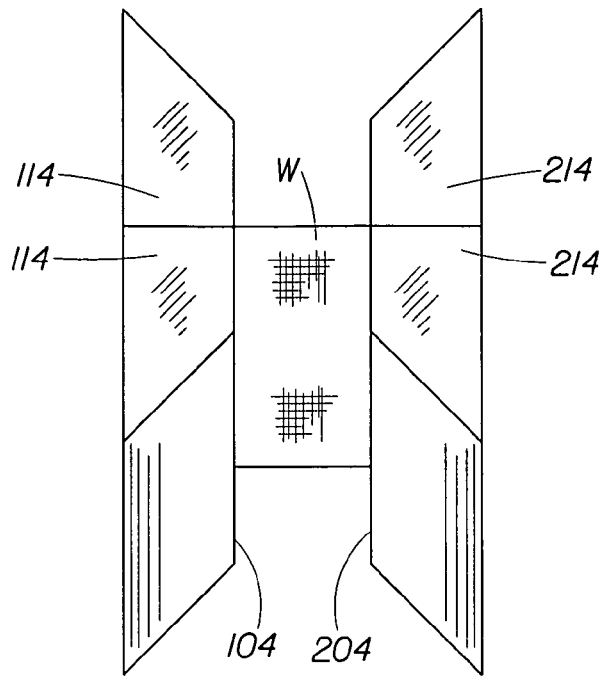
Figure 8D:
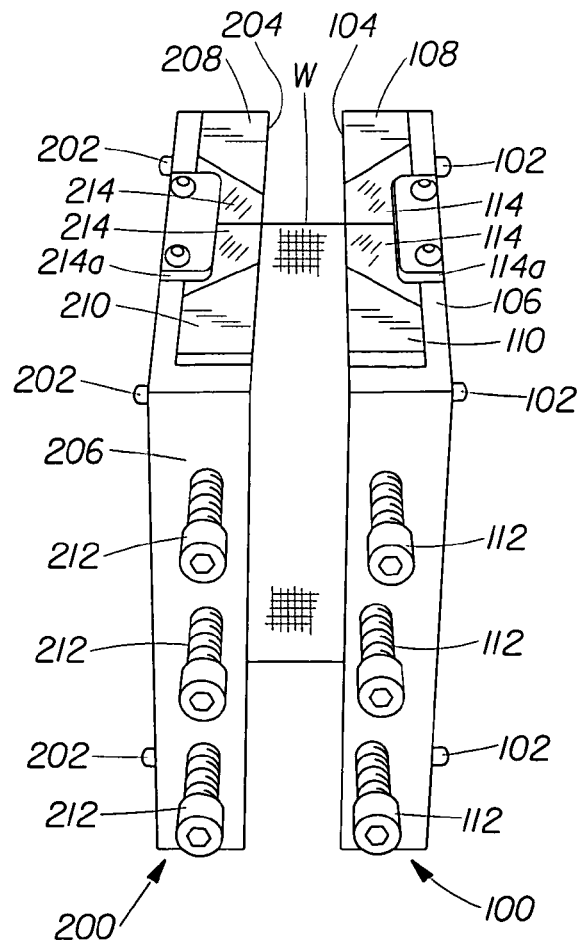

Also prior to running the tensile test, an engineer/technician defines the following parameters: gauge length Lo of the workpiece W, i.e., the taut but unstretched length of the workpiece W extending from an outer surface 104 of the first gripping device 100 to an outer surface 204 of the second gripping device 200, see FIG. 8C; a desired substantially constant strain rate (1/seconds) to which the workpiece W will be subjected during the test run; distance "Pli," noted above; and the final distance the carriage 30 is spaced from the bumpers 50, e.g., 75 mm.

The carriage 30 is then moved to a position such that the distance between the outer surface 104 of the first gripping device 100 and the outer surface 204 of the second gripping device 200 is less than the gauge length Lo of the workpiece W. The workpiece W and the engaging members 114 and 214 are then loaded between and clamped by the gripping device members 108, 110 and 208, 210.

Thereafter, the carriage 30 is moved to a start position, also its home position, where the outer surface 204 of the second gripping device 200 is spaced a distance Pli away from the outer surface 104 of the first gripping device 100. The distance "Pli" is selected such that sufficient space is provided between the gripping devices 100 and 200 so that the workpiece W is not overly compressed and damaged by the gripping devices 100 and 200. The distance "Pli" may be equal to a predefined value times the initial gauge length of the workpiece W, e.g., $Pli = 0.10 \times L_0$.

It is contemplated that the workpiece W may be heated to a predefined temperature prior to conducting the test run by moving the second gripping device 200 so that it is spaced the distance Pli from the first gripping device 100. As noted above, the heater controller 320 maintains the heated plates 38 and 82 at a predefined temperature. The workpiece W can be heated to a desired temperature by maintaining the workpiece W between the first and second gripping devices 100 and 200 for a predefined period of time with the heated plates 38 and 82 controlled to a predetermined temperature.

To effect the test run, the controller 300 causes the motors 40 to drive the carriage 30 from a start position (also its "home" position), where the second gripping device 200 is spaced the distance Pli from the first gripping device 100, in a direction away from the first gripping device 100 such that a tensile load is applied to the workpiece W. The controller 300 causes the motors 40 to continue to drive the carriage 30 until it reaches a final position where it is spaced a predefined distance, e.g., 75 mm away from the bumpers 50. When the carriage 30 is at its final position, the second gripping device 200 is also at its stop or final position and is spaced a distance P3f away from the first gripping device 100. During movement of the carriage 30, the workpiece W stretches until the tensile load causes it to fail, i.e., break, or until the carriage 300 reaches its final position. In the illustrated embodiment, movement of the carriage 30 from its start or home position to its final position is separated into three discrete segments: a forward acceleration segment; a constant velocity segment; and a reverse acceleration segment.

Each of the three segments comprises a plurality of equal discrete time intervals, e.g., 300 microseconds. For example, the total time period T required for execution of the three segments is determined, as discussed below, and this total time period is then divided by a predefined number of control points the drive controller 300 is capable of processing during a tensile test run, e.g., 7990, so as to determine the period for the discrete time intervals. If the calculated period for the discrete time intervals is less than a predefined value, e.g., 300 microseconds, the predefined value is used.

Using equations corresponding to the three segments, to be discussed below, a processor/memory unit 340 determines, for each discrete time interval within each segment, a corresponding position for the carriage 30. The time intervals and corresponding carriage positions are provided to the drive controller 300. During the forward acceleration segment, the constant velocity segment and the reverse acceleration segment, the drive controller 300 generates appropriate drive signals to the amplifiers 360a, 360b to control the movement of the carriage 30 based on the predefined carriage positions corresponding to the discrete time intervals for those segments, and in response to carriage position signals from the linear encoder read head 410 and force signals fed back from the amplifier 84b. Because no load is applied by the workpiece W to the carriage 30 during the forward acceleration segment, and the workpiece W has typically failed by the start of the reverse acceleration segment, such that no load is applied by the workpiece W to the carriage 30 during that segment, the force signals fed back from the amplifier 84b during those two segments are typically indicative of a 0 force.

The processor/memory unit 340 calculates the total time period T required for execution of the three segments using the following equation:

$$T=T_1+T_2+T_3$$

where $T_1$=the total time during the forward acceleration segment;

$T_2$=the total time during the constant velocity segment; and $T_3$=the total time during the reverse acceleration segment.

The equations for determining $T_1$; $T_2$; and $T_3$ are set out below.

The unit 340 then divides the total time T by the combined number of control points for all three segments, e.g., 7990, so as to determine the time period for the discrete time intervals.

The forward acceleration segment is defined as occurring from when the second gripping device 200, positioned a distance Pli away from the first gripping device 100, is initially moved away from the first gripping device 100 until the carriage 30 reaches a predefined velocity value $V_2$, which velocity value is the one maintained during the constant velocity segment. The length of the workpiece W between the first and second gripping devices 100 and 200 is equal to its initial gauge length Lo at the end of the forward acceleration segment such that a tensile load is not applied to the workpiece W until the beginning of the constant velocity segment.

The controller 300, with the workpiece W clamped between the two gripping devices 100 and 200, causes the carriage 30 to move in accordance with predetermined carriage positions $P_1$ corresponding to each of the discrete time intervals occurring during the forward acceleration segment. Those carriage positions $P_1$ are predetermined by the processor/memory unit 340 and thereafter provided to the controller 300. The processor/memory unit 340 also determines corresponding carriage velocity values and carriage acceleration values, which are provided to the controller 300. The processor/memory unit 340 calculates a carriage position, a carriage velocity and a carriage acceleration for each of the plurality of equal discrete time intervals occurring during the forward acceleration segment using the equations that follow:

Acceleration $A_1$ in the forward acceleration segment:

$$A_1=V_2/T_1$$

where:

$V_2$=Lo×dε/dt (velocity in the constant velocity segment);
Lo=the initial gauge length of the workpiece W;
ε=Engineering strain;
dε/dt=the desired constant rate of strain to which the workpiece W will be subjected during the test run;

$$T_1 = \frac{2 \times (L_0 - Pli)}{V_2}$$

(the total time during the forward acceleration segment);

Pli=the distance the second gripping device 200 is spaced from the first gripping device 100 at the beginning of the test run.

Velocity $V_1$ in the forward acceleration segment:

$$V_1=A_1\times t_1$$

where:

$t_1$=0 to $T_1$

Position in the forward acceleration segment:

$$P_1 = Pli + \frac{(A_1 \times t_1^2)}{2}$$

where $t_1$=0 to $T_1$;

$P_1$=the carriage position (or position of the second gripping device 200) relative to the first gripping device 100 and corresponding to time $t_1$;

Pli=the distance the second gripping device 200 is spaced from the first gripping device 100 at the beginning of the test run; and $A_1$=see the equation for carriage acceleration in the forward acceleration segment above.

The constant velocity segment is defined as occurring from the forward acceleration segment until the carriage velocity begins to decrease during the reverse acceleration segment. During the constant velocity segment, the carriage 30 is maintained at a substantially constant velocity $V_2$. During this segment, a tensile load is applied to the workpiece W such that the workpiece W experiences a substantially constant rate of strain, which rate of strain is preselected by the engineer/technician. The controller 300 causes the carriage 30 to move in accordance with predetermined carriage positions $P_2$ corresponding to each of the discrete time intervals occurring during the constant velocity segment. Those carriage positions $P_2$ are predetermined by the processor/memory unit 340 and thereafter provided to the controller 300. The processor/memory unit 340 also determines corresponding carriage velocity values, which are provided to the controller 300. The processor/memory unit 340 calculates a carriage position and a carriage velocity for each of the plurality of equal discrete time intervals occurring during the constant velocity segment using the follows equations:

Acceleration $A_2$ in the constant velocity segment is always equal to 0.

Velocity $V_2$ during the constant velocity segment:

$$V_2=Lo\times d\epsilon/dt$$

Lo=the initial gauge length of the workpiece W; and
dε/dt=the desired constant rate of strain to which the workpiece W will be subjected during the test run.

Position in the constant velocity segment:

$$P_2=V_2\times t_2$$

where:

$P_2$=the carriage position (or position of the second gripping device 200) relative to the position of the carriage 30 at the beginning of the constant velocity segment and corresponding to time $t_2$;

$t_2$=0 ("0" time is at the beginning of the constant velocity segment) to $T_2$; and $T_2$=total time in the constant velocity segment;

$$T_2 = \frac{P3f - Pli - \left(\frac{A_1 \times T_1^2}{2}\right) + \left(\frac{A_3 \times T_3^2}{2}\right)}{V_2}$$

P3f=the final position of the second gripping device 200 at the end of the reverse acceleration segment relative to the first gripping device 100;

Pli=the distance the second gripping device 200 is spaced from the first gripping device 100 at the beginning of the test run;

$A_1$ is equal to the acceleration in the forward acceleration segment;

$T_1$ is equal to the total time in the forward acceleration segment;

$V_2$ is equal to the velocity in the constant velocity segment;

$A_3$ is equal to the acceleration during the reverse acceleration segment, see equation below; and $T_3$ is equal to the total time in the reverse acceleration segment, see equation below.

The reverse acceleration segment is defined as occurring from the end of the constant velocity segment until when the carriage 30 reaches its final or stop position. The controller 300 causes the carriage 30 to move in accordance with predetermined carriage positions $P_3$ corresponding to each of the discrete time intervals occurring during the reverse acceleration segment. Those carriage positions $P_3$ are predetermined by the processor/memory unit 340 and thereafter provided to the controller 300. The processor/memory unit 340 also determines corresponding carriage velocity values and carriage acceleration values, which are provided to the controller 300. The processor/memory unit 340 calculates a carriage position, a carriage velocity and a carriage acceleration for each of the plurality of equal discrete time intervals occurring during the reverse acceleration segment using the follows equations:

Acceleration $A_3$ in the reverse acceleration segment:

$$A_3 = -V_2/T_1$$

where:

$V_2$=Lo×dε/dt (velocity in the constant velocity segment);

Lo=the initial gauge length of the workpiece W;

dε/dt=the desired constant rate of strain to which the workpiece W will be subjected during the test run;

$$T_1 = \frac{2 \times (L_0 - Pli)}{V_2}$$

(the total time during the forward acceleration segment, which equals to the total time during the reverse acceleration segment);

Pli=the distance the second gripping device 200 is spaced from the first gripping device 100 at the beginning of the test run.

Velocity $V_3$ in the reverse acceleration segment:

$$V_3 = V_2 + (A_3 \times t_3)$$

where:

$t_3$=0 ("0" time is at the beginning of the reverse acceleration segment) to T3;

$T_3$=total time in the reverse acceleration segment, which equals T1.

Position in the reverse acceleration segment:

$$P_3 = -\left[\frac{(A_3 \times t_3)}{2}\right]$$

where:

$P_3$=the carriage position (or position of the second gripping device 200) relative to the position of the carriage 30 at the beginning of the reverse acceleration segment and corresponding to time $t_3$;

$t_3$=0 ("0" time is at the beginning of the reverse acceleration segment) to $T_3$;

$T_3$=total time in the reverse acceleration segment, which equals $T_1$; and $A_3$=see the equation above for $A_3$.

With the carriage 30 at its start or home position, the controller 300 causes the servo linear motors 40 to drive the carriage 30 away from the first gripping device 100 such that the carriage 30 is accelerated to velocity $V_2$. In generating appropriate drive signals to the amplifiers 360a, 360b during this segment, the controller 300 takes into consideration position feedback information from the linear encoder read head 410 such that it compares the actual position of the carriage 30 determined from the position information provided by the read head 410 to the predefined, desired positions. The controller 300 also takes into consideration force or load information generated by the load cells 84 in generating appropriate drive signals to the amplifiers 360a, 360b during the forward acceleration segment. However, because no load is applied by the workpiece W to the carriage 30, or vice versa, during the forward acceleration segment, the force signals fed back from the amplifier 84b during this segment are typically indicative of a 0 force.

The controller 300 further causes the carriage 30 to travel at the velocity $V_2$ throughout the constant velocity segment. In generating appropriate drive signals to the amplifiers 360a, 360b during the constant velocity segment, the controller 300 takes into consideration position feedback information from the linear encoder read head 410 such that it compares the actual position of the carriage 30 determined from the position information provided by the read head 410 to the predefined, desired positions. The controller 300 also takes into consideration force or load information generated by the load cells 84 in generating appropriate drive signals to the amplifiers 360a, 360b during the constant velocity segment.

Starting at the beginning of the reverse acceleration segment, the controller 300 causes the carriage 30 to decelerate from the velocity $V_2$ to a zero velocity, at which point the carriage 30 is at its final or stop position. In generating appropriate drive signals to the amplifiers 360a, 360b during the reverse acceleration segment, the controller 300 takes into consideration position feedback information from the linear encoder read head 410 such that it compares the actual position of the carriage 30 determined from the position information provided by the read head 410 to the predefined, desired positions. The controller 300 also takes into consideration force or load information generated by the load cells 84 in generating appropriate drive signals to the amplifiers 360a, 360b during the reverse acceleration segment. However, because the workpiece W typically fails during the prior segment, no load is typically applied by the workpiece W to the carriage 30, or vice versa, and, hence, the force signals fed back from the amplifier 84b during this segment are typically indicative of a 0 force.

Figure 9:
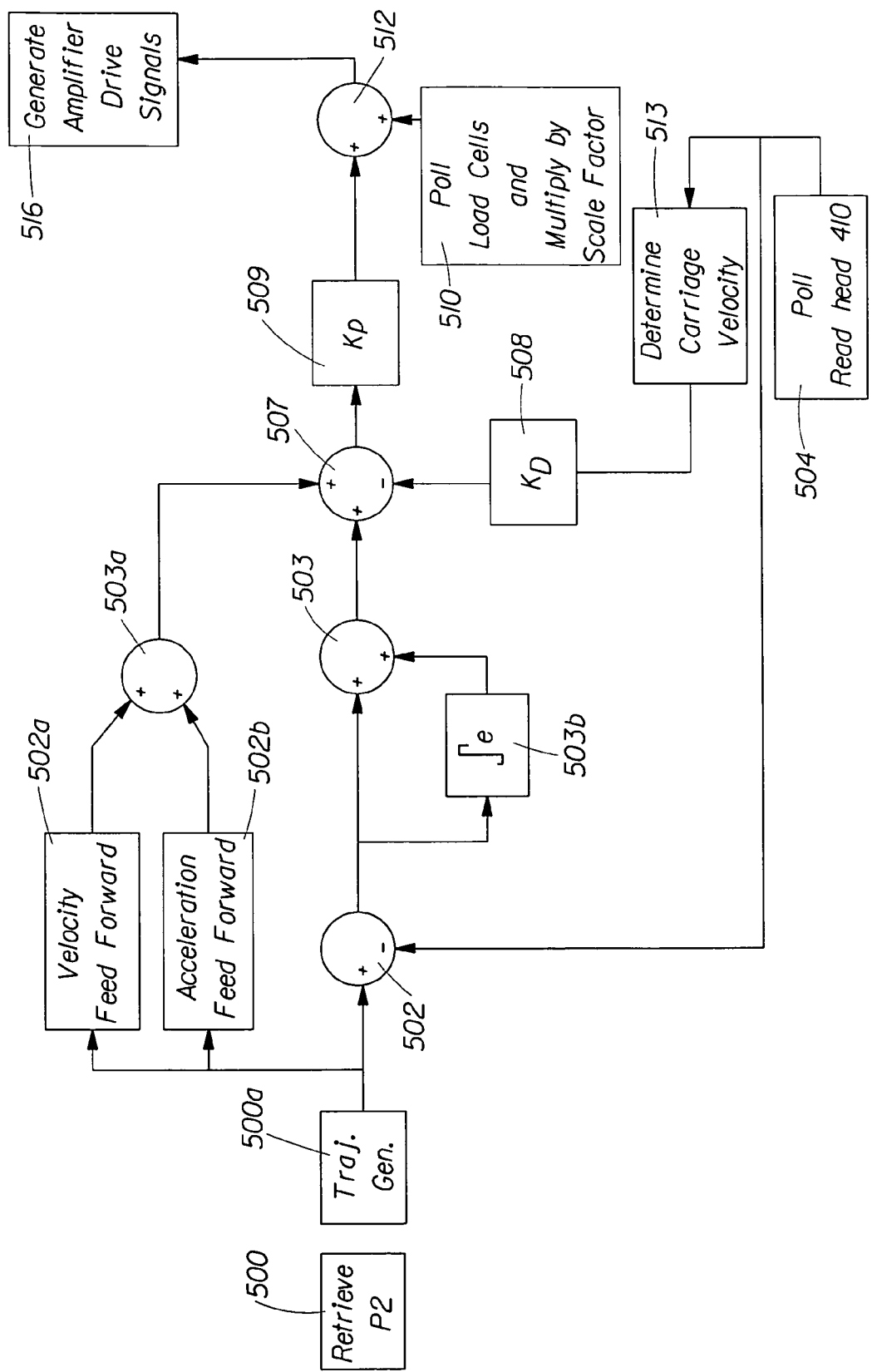
FIG. 9 is a block diagram illustrating steps taken by a controller of the apparatus of FIG. 1 in processing force feedback from load cells while controlling the position of the carriage as a function of time during a constant velocity segment.

It was found that the accuracy of the control of the position of the carriage as a function of time by the controller 300 could be enhanced by using force feedback from the load cells 84. A characteristic block diagram is illustrated in FIG. 9 showing steps taken by the controller 300 in accordance with a servo-controller algorithm involving processing force feedback from the load cells 84 while controlling the position of the carriage 30 as a function of time.

At step 500, the controller 300 retrieves serially the desired carriage positions $P_2$, predetermined by the processor/memory unit 340 and previously provided to the controller 300, for the discrete time intervals occurring during each segment. Each of the discrete time intervals occurring during the forward and reverse acceleration segments and the constant velocity segment comprises the same first time period $TP_1$. During step 500a, termed a "trajectory generator" step, the controller 300 interpolates between the carriage positions $P_2$, i.e., coarse carriage positions, generated at the discrete time intervals, each comprising the first period $TP_1$, such that fine carriage positions $P_{2F}$ are generated at second time intervals, each comprising a second time period $TP_2$, which is less than the first period $TP_1$.

At step 502, the controller 300 generates a position error value by comparing the fine carriage positions $P_{2F}$ to measured carriage positions. Each measured carriage position is determined using data acquired by polling the linear encoder read head 410, see step 504. At step 503, the current position error is combined, via addition, with its integrated value determined during step 503b. The integration of the position error occurring during step 503b provides a method by which the controller 300 can force the position error to zero, i.e., the controller 300 continuously accumulates the position error and adds the accumulated error back into the current position error.

The fine carriage positions $P_{2F}$ determined during step 500a are used in step 502a to generate a velocity feedforward signal. During step 502a, the controller 300 determines the first derivative of the fine carriage positions $P_{2F}$ with respect to the time base of the servo-controller algorithm, which time base comprises discrete time intervals, each having a period equal to the second period $TP_2$ noted above. The velocity feedforward signal is typically used to compensate for mechanical damping, i.e., friction, present in the apparatus 10. The fine carriage positions $P_{2F}$ determined during step 500a are also used in step 502b to generate an acceleration feedforward signal, wherein the controller 300 takes the second derivative of the fine carriage positions $P_{2F}$ with respect to the time base of the servo-controller algorithm, which time base comprises discrete time intervals, each having a period equal to the second period $TP_2$ noted above. The acceleration feedforward signal is typically used to compensate for the system inertia. At step 503a the velocity and acceleration feedforward signals are summed together.

The velocity of the carriage 30 is determined during step 513 by taking the first derivative of the actual position values received from the encoder read head 410. The first derivative or carriage velocity values are multiplied by a derivative gain value during step 508 so as to provide damping for stability in the controller 300. At step 507, the output from step 508 is subtracted from the sum determined during step 503 as well as the sum determined during step 503a. The output from step 507 is multiplied by a gain factor during step 509 to provide a desired response for the motors 40, such that the time, overshoot, and general bandwidth of the controller 300 can be adjusted for the desired response. In this case the preferred response regarding movement of the carriage 30 to a desired position $P_2$ consists of minimizing the position error, minimizing overshoot in the positioning of the carriage 30, and achieving the desired position $P_2$ in a minimal amount of time.

The output from step 509 is typically referred to as a current reference value, and normally is provided directly to a motor current generator algorithm in the controller 300, which algorithm comprises a current control loop. However, in accordance with the present invention, the controller 300, at step 510, polls the load cell amplifier 84b and generates a tensile load value directly proportional to the load sensed by the load cells 84, i.e., the tensile force applied by the carriage 30 to the workpiece W. The controller 300 then multiplies the tensile load value by a scale factor so as to convert the raw signal from the load cell amplifier 84b to a scaled value representing a motor current directly proportional to the force applied by the motors 40 to the carriage 30 causing the tensile load on the workpiece W. This scaled tensile load value is added to the current reference value at step 512 to generate a value that represents the actual force required by the motors 40 to move the carriage 30 to the next desired position $P_2$, as defined by the output from step 509, as well as the motor force required to generate the tensile load on the workpiece W, as represented by the output from step 510. At step 516, using a current loop, the controller 300 determines an appropriate drive signal for the first and second amplifiers 360a and 360b based on the output from step 512. The current loop is typically configured from the motors' electrical characteristics, and modified so as to provide a desired current response. The desired current response in this embodiment is minimal current overshoot, at the fastest achievable rate to the output from step 512.

By utilizing the scaled tensile load value with the current reference value at step 512, the controller 300 effectively bypasses the position, velocity and acceleration loops in steps 502, 502a and 502b with regard to changes in the load applied by the carriage 30 to the workpiece W so as to more directly take into consideration tensile load variations when determining the drive signals for the first and second amplifiers 360a and 360b, thereby directly enhancing the accuracy of the control of the position of the carriage 30 as a function of time. It is also noted that when the load value is taken into consideration, the controller response time for controlling the operation of the motors 40 and, hence, the position of the carriage 30 as a function of time, is improved. That is, without taking into consideration the load value sensed by the load cells during step 512, changes in the tensile load applied by the workpiece W to the carriage 30, or vice versa, would have to be indirectly taken into consideration by the position, velocity and acceleration control loops. Doing so would reduce the response time of the controller 300 in controlling the operation of the motors 40 such that the accuracy of the control of the carriage position by the controller 300 would be negatively affected, especially at high speeds when the load applied by the workpiece W to the carriage 30 and vice versa changes rapidly.

It is further contemplated that first and second constant velocity segments may be defined for any given test run. In such a case, the predefined carriage positions for the first constant velocity segment are defined such that the carriage 30 operates at a substantially constant first velocity during that segment, and the predefined carriage positions for the second constant velocity segment are defined such that the carriage 30 operates at a substantially constant second velocity during the second constant velocity segment. The first and second velocities are not equal to one another. An additional acceleration segment, so as to increase or decrease the velocity of the carriage 30, is provided between the first and second constant velocity segments. In this embodiment, the workpiece W experiences a predefined substantially constant first rate of strain during movement of the second gripping device 200 at the first velocity and the workpiece W experiences a predefined substantially constant second rate of strain during movement of the second gripping device 200 at the second velocity. The first rate of strain differs from the second rate of strain.

It is also contemplated that the controller 300 may store the position information provided by the read head 410 and the load information generated by the load cells 84 for any given test run for subsequent review and processing. From that information, the controller 300 may generate the following additional data: carriage position by time; and load applied to the workpiece W by time; and load applied to the workpiece W by carriage position.

During each test run, the carriage 30 experiences "jerk" or mechanical vibrations due to changes in the carriage acceleration. This vibrational noise can be determined by running a "dry" test run, i.e., a test run without a workpiece W. During the dry test run, the load cell data from the load cell amplifier 84b is collected as a function of time and carriage position. After each actual test run, i.e., a test run involving a workpiece W placed under a tensile load, the data from that actual test run is compared to the data collected from the dry test run, i.e., the data from the dry test run is subtracted from the data from the actual test run, such that the vibrational noise is removed.

It is additionally contemplated that the carriage 30 may be accelerated to the velocity $V_2$ prior to the workpiece W being in a taut condition. However, the constant rate of strain would only occur after a tensile load is applied to the workpiece W, i.e., after the workpiece is in a taut condition between the first and second gripping devices 100 and 200.

Figure 11A:
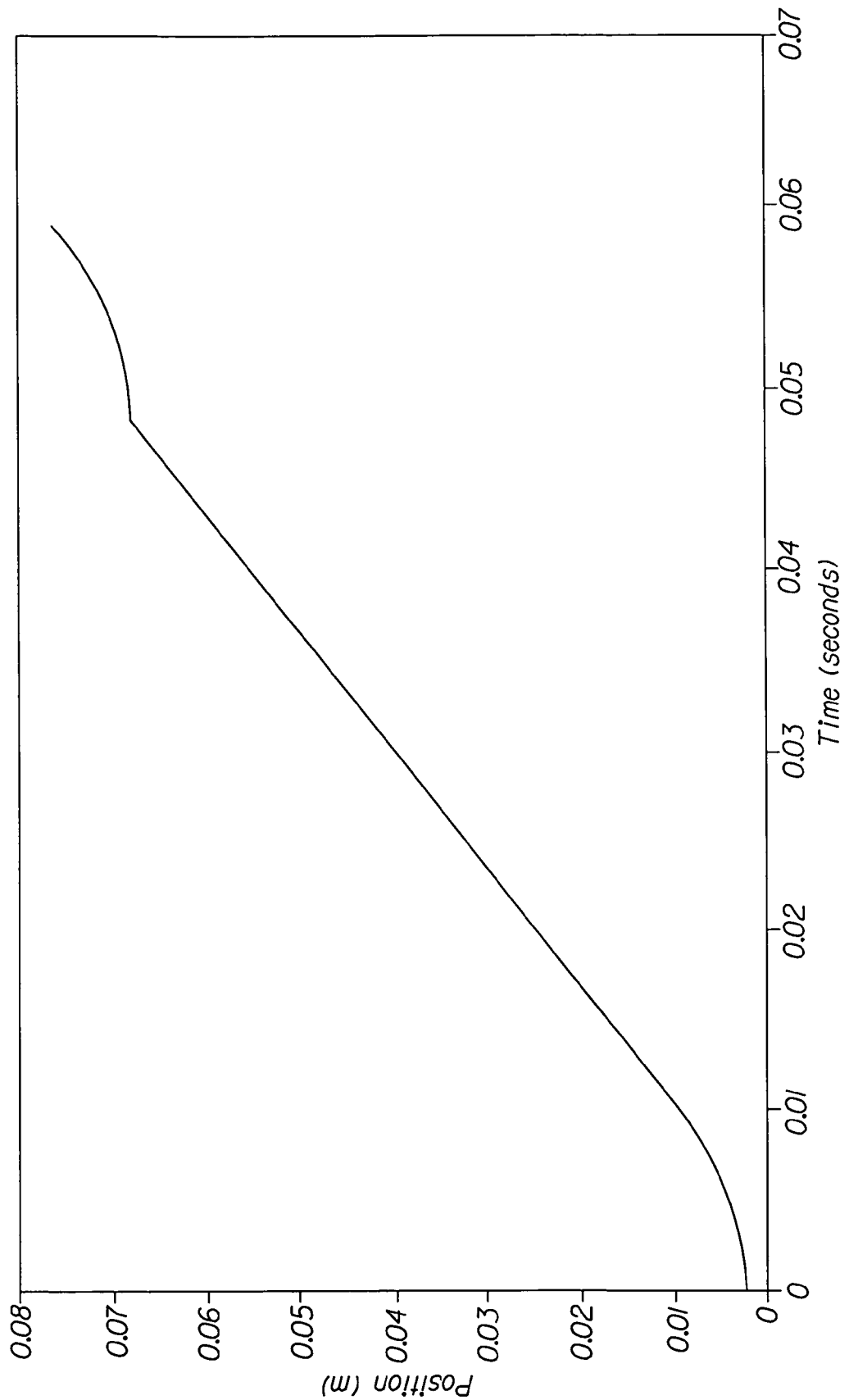
FIG. 11A is a plot of a position by time profile for the Example.
Figure 11B:
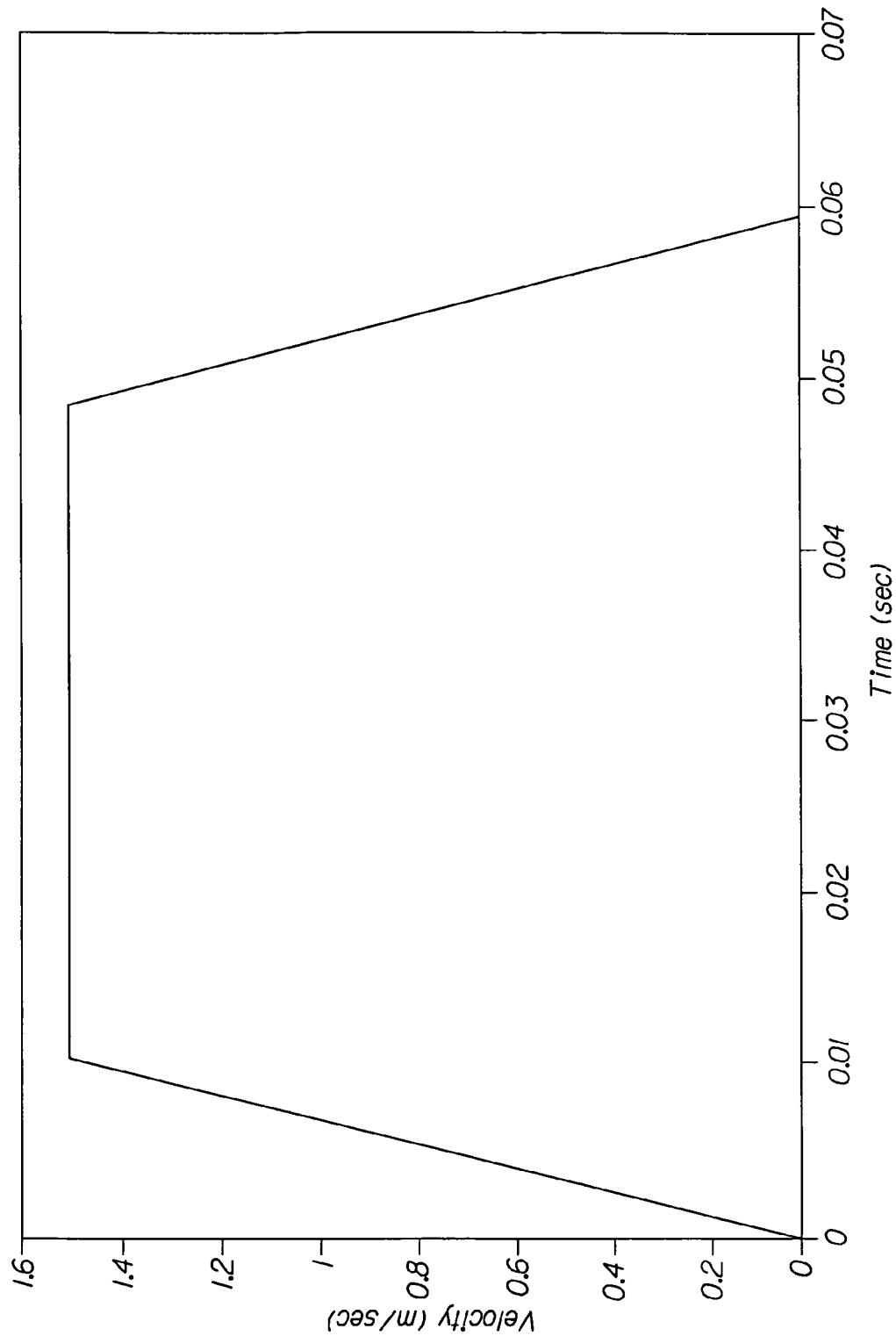
FIG. 11B is a plot of a velocity by time profile for the Example.
Figure 11C:
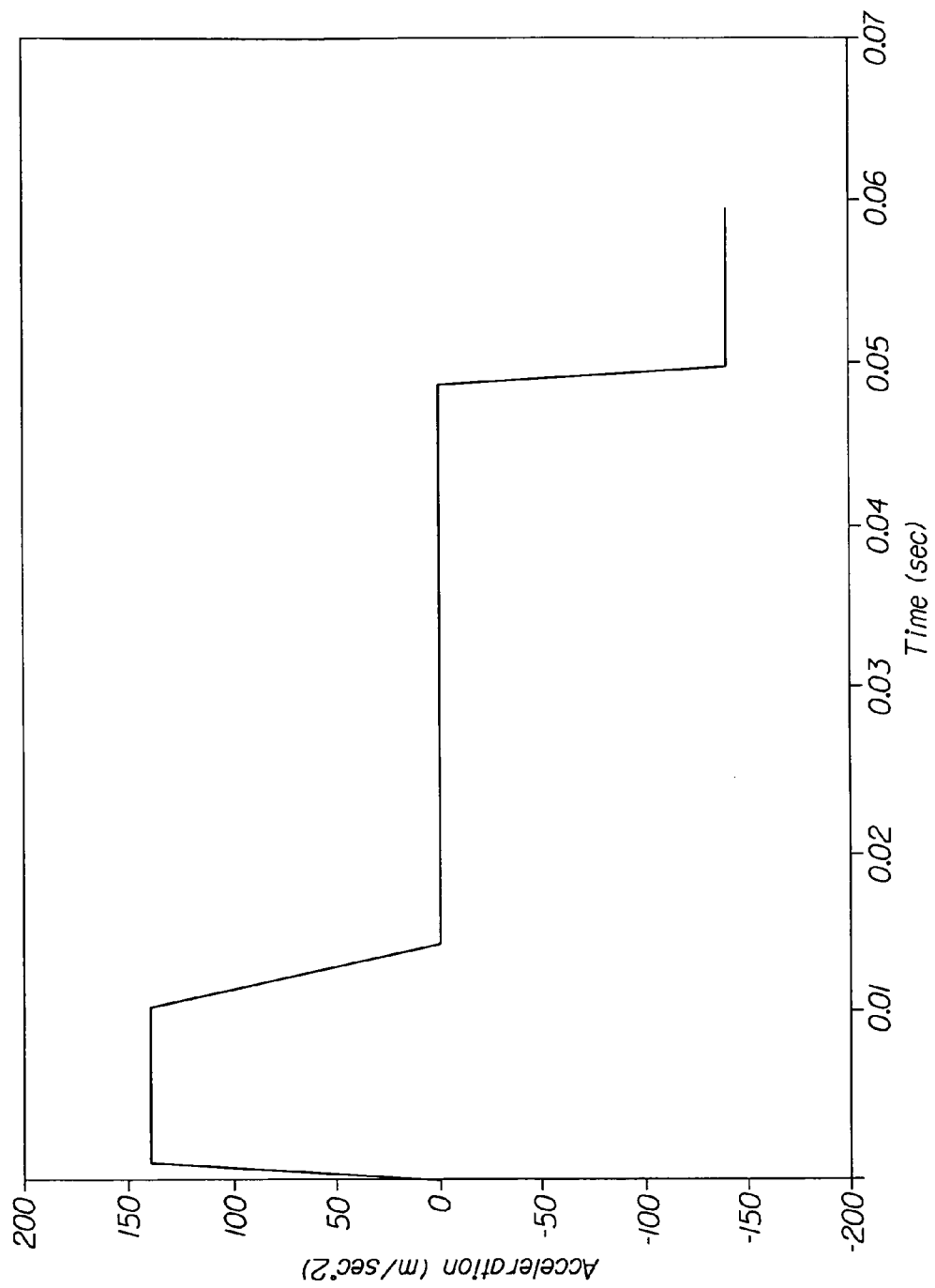
FIG. 11C is a plot of an acceleration by time profile for the Example.

Data from an Example tensile test run is set out below. A position by time profile for the Example is illustrated in FIG. 11A; a velocity by time profile for the Example is illustrated in FIG. 11B; and an acceleration by time profile for the Example is illustrated in FIG. 11C.

Data from Example

| Motion Control Model for Tensile Test Program | | | | | |
|---|---|---|---|---|---|
| Strain Rate (sec^-1) | | | | | 150.0 |
| Initial Gage Length (m) | | | | | 0.010 |
| Initial Position in Forward Acceleration Segment (m) | | | | | 0.002 |
| Final Position in Reverse Acceleration Segment (m) | | | | | 0.075 |
| The above numbers are defined by the user | | | | | |
| Time in Segment (sec) | Position in Segment (m) | Total Time (sec) | Total Position (m) | Velocity (m/sec) | Acceleration (m/sec^2) |
| Forward Acceleration Segment | | | | | |
| 0 | 0.0020 | 0.00000 | 0.0020 | 0.000 | 0.00 |
| 0.00107 | 0.0021 | 0.00107 | 0.0021 | 0.150 | 140.63 |
| 0.00213 | 0.0023 | 0.00213 | 0.0023 | 0.300 | 140.63 |
| 0.00320 | 0.0027 | 0.00320 | 0.0027 | 0.450 | 140.63 |
| 0.00427 | 0.0033 | 0.00427 | 0.0033 | 0.600 | 140.63 |
| 0.00533 | 0.0040 | 0.00533 | 0.0040 | 0.750 | 140.63 |
| 0.00640 | 0.0049 | 0.00640 | 0.0049 | 0.900 | 140.63 |
| 0.00747 | 0.0059 | 0.00747 | 0.0059 | 1.050 | 140.63 |
| 0.00853 | 0.0071 | 0.00853 | 0.0071 | 1.200 | 140.63 |
| 0.00960 | 0.0085 | 0.00960 | 0.0085 | 1.350 | 140.63 |
| 0.01067 | 0.0100 | 0.01067 | 0.0100 | 1.500 | 140.63 |
| Constant Velocity Segment | | | | | |
| 0 | 0 | 0.01067 | 0.0100 | 1.500 | 0.00 |
| 0.00380 | 0.0057 | 0.01447 | 0.0157 | 1.500 | 0.00 |
| 0.00760 | 0.0114 | 0.01827 | 0.0214 | 1.500 | 0.00 |
| 0.00320 | 0.0048 | 0.01387 | 0.0148 | 1.500 | 0.00 |
| 0.00427 | 0.0064 | 0.01493 | 0.0164 | 1.500 | 0.00 |
| 0.00533 | 0.0080 | 0.01600 | 0.0180 | 1.500 | 0.00 |
| 0.00640 | 0.0096 | 0.01707 | 0.0196 | 1.500 | 0.00 |
| 0.00747 | 0.0112 | 0.01813 | 0.0212 | 1.500 | 0.00 |
| 0.00853 | 0.0128 | 0.01920 | 0.0228 | 1.500 | 0.00 |
| 0.00960 | 0.0144 | 0.02027 | 0.0244 | 1.500 | 0.00 |
| 0.03800 | 0.0570 | 0.04867 | 0.0670 | 1.500 | 0.00 |
| Reverse Acceleration Segment | | | | | |
| 0 | 0 | 0.04867 | 0.0670 | 1.500 | 0.00 |
| 0.00107 | 0.0001 | 0.04973 | 0.0671 | 1.350 | −140.63 |
| 0.00213 | 0.0003 | 0.05080 | 0.0673 | 1.200 | −140.63 |
| 0.00320 | 0.0007 | 0.05187 | 0.0677 | 1.050 | −140.63 |
| 0.00427 | 0.0013 | 0.05293 | 0.0683 | 0.900 | −140.63 |
| 0.00533 | 0.0020 | 0.05400 | 0.0690 | 0.750 | −140.63 |

-continued

| \multicolumn{6}{c}{Motion Control Model for Tensile Test Program} |
| --- | --- | --- | --- | --- | --- |
| 0.00640 | 0.0029 | 0.05507 | 0.0699 | 0.600 | −140.63 |
| 0.00747 | 0.0039 | 0.05613 | 0.0709 | 0.450 | −140.63 |
| 0.00853 | 0.0051 | 0.05720 | 0.0721 | 0.300 | −140.63 |
| 0.00960 | 0.0065 | 0.05827 | 0.0735 | 0.150 | −140.63 |
| 0.01067 | 0.0080 | 0.05933 | 0.0750 | 0.000 | −140.63 |

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A simulation apparatus comprising:
a fixed main body;
a carriage associated with said main body for movement relative to said main body;
a first device coupled to said fixed main body for engaging a workpiece;
a second device coupled to said carriage for movement with said carriage, said second device also engaging said workpiece;
at least one motor apparatus coupled to said fixed main body and said carriage for effecting movement of said carriage and said second device relative to said main body such that a tensile load is applied to said workpiece;
sensor apparatus comprising at least one force sensor for sensing the tensile load applied to said workpiece during the movement of said second device; and
a drive controller coupled to said at least one motor apparatus for controlling the operation of said at least one motor apparatus in accordance with predefined carriage positions corresponding to discrete time intervals and in response to feedback from said sensor apparatus comprising said at least one force sensor.

2. A simulation apparatus as set forth in claim 1, wherein at least a portion of said predefined carriage positions are selected such that said carriage moves at a substantially constant velocity during at least a portion of its movement between a start position and a stop position.

3. A simulation apparatus as set forth in claim 1, wherein a first portion of said predefined carriage positions are selected such that said carriage operates at a substantially constant first velocity during a first portion of its movement between a start position and a stop position and a second portion of said predefined carriage positions are selected such that said carriage operates at a substantially constant second velocity during a second portion of its movement between the start position and the stop position, said second velocity being different from said first velocity.

4. A simulation apparatus as set forth in claim 1, wherein said predefined carriage positions are defined such that said workpiece experiences a predefined substantially constant rate of strain while said tensile load is applied to said workpiece.

5. A simulation apparatus as set forth in claim 1, wherein said at least one motor apparatus comprises at least one servo linear motor.

6. A simulation apparatus as set forth in claim 5, wherein said at least one motor apparatus further comprises at least one amplifier which is coupled to said drive controller and said at least one servo linear motor.

7. A simulation apparatus as set forth in claim 1, wherein said carriage reciprocates linearly relative to said fixed main body.

8. A simulation apparatus as set forth in claim 1, wherein said first device is coupled to said fixed main body via a coupling structure, said coupling structure including said at least one force sensor, said controller increasing a drive signal to said at least one motor apparatus in response to the load sensed by said at least one force sensor.

9. A simulation apparatus as set forth in claim 8, wherein said at least one force sensor comprises at least one load cell.

10. A simulation apparatus as set forth in claim 9, wherein said sensor apparatus further comprises a linear encoder read head coupled to said fixed main body and a sensor strip coupled to said carriage, said read head reading position values from said sensor strip and generating corresponding signals to said controller.

11. A simulation apparatus as set forth in claim 10, wherein said controller controls the operation of said at least one motor apparatus based on said carriage positions and in response to the signals generated by said read head and said at least one load cell.

12. A simulation apparatus as set forth in claim 11, wherein said carriage positions occurring during a constant velocity segment are determined via the following equation:

$$P2 = (Lo \times d\epsilon/dt)(t)$$

where Lo=an initial gauge length of said workpiece;
t=0 to T (time at the end of the constant velocity segment)
dε/dt=strain rate.

13. A simulation apparatus as set forth in claim 8, wherein said coupling structure further comprises:
a first cooling plate;
a first heated plate coupled to said first cooling plate; and
said first device being coupled to said first heated plate.

14. A simulation apparatus as set forth in claim 13, wherein said at least one load cell is positioned between said first cooling plate and said first heated plate and said tensile load applied to said workpiece is transferred to said at least one load cell via said first device and said first heated plate.

15. A simulation apparatus as set forth in claim 13, wherein said carriage comprises:
a carriage main body portion;
a second cooling plate coupled to said carriage main body portion; and
a second heated plate coupled to said second cooling plate, wherein
said second workpiece-engaging device is coupled to said second heated plate.

16. A method of applying a tensile load to a workpiece comprising the steps of:
    clamping the workpiece between a first, substantially fixed device and a second device coupled to a movable carriage so as to move with said carriage;
    providing at least one motor apparatus coupled to said carriage;
    moving said carriage via said at least one motor apparatus such that said second device moves in a direction away from said substantially fixed first device to apply a tensile load to said workpiece;
    sensing the tensile load applied to said workpiece during the movement of said carriage; and
    controlling the operation of said at least one motor apparatus in accordance with predefined carriage positions corresponding to discrete time intervals and in response to the sensed tensile load.

17. A method as set forth in claim 16, wherein said second device is moved such that said workpiece experiences a predefined substantially constant rate of strain.

18. A method as set forth in claim 16, further comprising the step of accelerating said second device to a first velocity and thereafter accelerating said second device to a second velocity, said workpiece experiencing a predefined substantially constant first rate of strain while a first tension load is applied to said workpiece during movement of said second device at said first velocity and said workpiece experiencing a predefined substantially constant second rate of strain while a second tension load is applied to said workpiece during movement of said second device at said second velocity, said first rate of strain differing from said second rate of strain.

* * * * *

UNITED STATES PATENT AND TRADEMARK OFFICE
CERTIFICATE OF CORRECTION

PATENT NO. : 7,062,983 B2 Page 1 of 1
APPLICATION NO. : 10/422879
DATED : June 20, 2006
INVENTOR(S) : Barry Jay Anderson et al.

It is certified that error appears in the above-identified patent and that said Letters Patent is hereby corrected as shown below:

Title Page

The title listed at (54), insert --A-- at the beginning of the title so it then reads: --A Simulation Apparatus.--

Column 1

Line 1, insert --A-- at the beginning of the title, so it then reads: --A Simulation Apparatus.--

Column 4

Line 10, delete "21" and insert -- 2I --.

Signed and Sealed this

Fourteenth Day of August, 2007

JON W. DUDAS
*Director of the United States Patent and Trademark Office*